United States Patent

Berg et al.

[11] 4,005,217
[45] Jan. 25, 1977

[54] TREATMENT OF HELMINTH INFECTIONS WITH SUBSTITUTED PHENYL-THIOUREA DERIVATIVES

[75] Inventors: Samuel Sidney Berg, Ilford; David Conwil Jenkins, Gidea Park; George Christopher James Martin; Ronald Frederick Phillipson, both of Brentwood; Garth Molesdale Thompson, Upminster, all of England

[73] Assignee: May & Baker Limited, England

[22] Filed: June 15, 1971

[21] Appl. No.: 153,407

[30] Foreign Application Priority Data

| June 26, 1970 | United Kingdom | 31209/70 |
| Dec. 11, 1970 | United Kingdom | 59111/70 |
| Mar. 25, 1971 | United Kingdom | 7850/71 |
| Apr. 1, 1971 | United Kingdom | 8462/71 |
| Apr. 1, 1971 | United Kingdom | 8466/71 |

[52] U.S. Cl. ............................ 424/300; 260/470
[51] Int. Cl.$^2$ ............................ A61K 31/27
[58] Field of Search ............ 424/300; 260/470

[56] References Cited

OTHER PUBLICATIONS

Teruhisa et al., Chem. Abst. vol. 73 (1970) p. 14523s.

Primary Examiner—Stanley J. Friedman
Attorney, Agent, or Firm—Stevens, Davis, Miller & Mosher

[57] ABSTRACT

Benzene derivatives of the formula:-

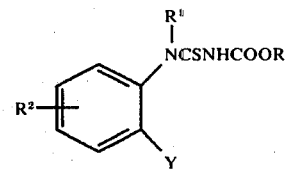

wherein R is an aliphatic hydrocarbon group of 1 to 4 carbon atoms optionally substituted by halogen or alkoxy, $R^1$ is hydrogen or methyl, $R^2$ is hydrogen, halogen, alkyl, alkanoylamino optionally substituted by cycloalkyl of 3 to 6 carbon atoms, alkoxycarbonylamino, alkanoyl, benzoyl or N-methylmethanesulphonylamino, and Y is primary amino or substituted amino, possess anthelmintic and anti-viral activity. New compounds within that formula possess fungicidal properties.

16 Claims, No Drawings

TREATMENT OF HELMINTH INFECTIONS WITH SUBSTITUTED PHENYL-THIOUREA DERIVATIVES

THIS INVENTION relates to benzene derivatives, compositions containing them and their use as anthelmintics, agricultural pesticides and anti-viral agents.

As a result of research and experimentation, it has now been found that the benzene derivatives of the general formula:-

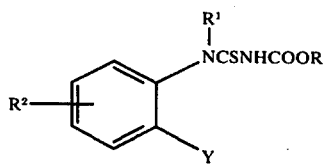

wherein R represents a straight- or branched-chain aliphatic hydrocarbon group containing not more than 4 carbon atoms which may be saturated or unsaturated, e.g. allyl or propargyl, and which may optionally be substituted by a halogen atom, e.g. chlorine, or an alkoxy group containing not more than 4 carbon atoms, $R^1$ represents a hydrogen atom or a methyl group, $R^2$ represents a hydrogen or a halogen atom, e.g. chlorine or fluorine, or a straight- or branched-chain alkyl group containing not more than 4 carbon atoms, an alkanoylamino group containing 1 to 4 carbon atoms in which the alkanoyl moiety may be straight- or branched-chain and may optionally be substituted by a cycloalkyl group containing from 3 to 6 carbon atoms, e.g. acetamido, cyclopropylcarbonamido or cyclohexylacetamido, an alkoxycarbonylamino group containing from 2 to 4 carbon atoms in which the alkoxy moiety may be straight- or branched-chain, a straight- or branched-chain alkanoyl group containing from 2 to 4 carbon atoms, a benzoyl group or a group $CH_3SO_2N(CH_3)-$, and Y represents a group $-NR^3R^4$ [wherein $R^3$ and $R^4$ each represent a hydrogen atom, or $R^3$ represents a hydrogen atom or a methyl group and $R^4$ represents a straight- or branched-chain alkanoyl group containing 1 to 4 carbon atoms (which may optionally be substituted by a cycloalkyl group containing from 3 to 6 carbon atoms), a straight- or branched-chain alkoxycarbonyl group containing 2 to 4 carbon atoms, or a group $-COAZ$ wherein A represents a straight chain aliphatic hydrocarbon group containing not more than 4 carbon atoms which may be saturated or unsaturated (e.g. a methylene, polymethylene or vinylene group) which may optionally be substituted by at least one methyl group, and Z represents a carboxy group or a group of the general formula:-

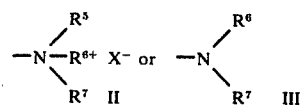

wherein $R^5$ represents a hydrogen atom or a straight- or branched-chain alkyl group containing not more than 4 carbon atoms, $R^6$ represents a hydrogen atom or a straight- or branched-chain alkyl group containing not more than 4 carbon atoms or a phenylalkyl group with 1 or 2 carbon atoms in the alkyl moiety, preferably benzyl, and $R^7$ represents a hydrogen atom or a straight- or branched-chain alkyl group containing not more than 4 carbon atoms, or $R^6$ and $R^7$ together with the nitrogen atom to which they are attached form a 5-, 6- or 7-membered heterocyclic ring which may contain in the ring one or two further hetero atoms selected from oxygen, nitrogen and sulphur and which may optionally be substituted by one or more straight- or branched-chain alkyl groups each containing not more than 6 carbon atoms, for example a pyrrolidin-1-yl, piperidino, morpholino, piperazin-1-yl or 4-alkylpiperazin-1yl, e.g. 4-methylpiperazin-1-yl, group and $X^-$ represents a pharmaceutically acceptable anion] and, where Y represents a primary amino group, acid addition salts thereof having a pharmaceutically acceptable anion, possess valuable chemotherapeutic properties, having, in particular, high anthelmintic and anti-viral activity.

When the compounds of general formula I can exist in stereoisomeric forms, all such isomers and their mixtures and racemates are included within the scope of the present invention.

The term 'pharmaceutically acceptable anion' means an anion which is relatively innocuous to the animal organism when used in therapeutic doses so that the beneficial properties of the cation are not vitiated by side-effects ascribable to the anion. Good examples of such anions are halide ions and the methanesulphonate ion.

According to a feature of the present invention, there is provided a method for the treatment of helminth infections in man and domestic animals, for example cattle, sheep, pigs, goats, poultry and equines, for example infections of the gastro-intestinal tract caused by parasitic nematode worms, for example members of the family Trichostrongylidae, in domestic animals, which comprises the administration of an anthelmintically effective amount of one or more compounds of general formula I. It is to be understood that reference in this Specification to compounds of general formula I for the treatment of helminth infections includes the use of pharmaceutically acceptable acid addition salts of those compounds of that formula wherein Y is a primary amino group.

The quantities of the compounds of formula I administered in the treatment of helminthiasis will vary with the species of animal treated, the nature and severity of the infection, the length of treatment and the method of administration. In general, the compounds are effective in treating helminthiasis when administered orally to domestic animals in dosages which may be as low as 5 mg/kg of animal body weight but which are preferably from about 25 mg/kg to about 250 mg/kg of animal body weight. Higher doses up to 500 mg/kg of animal body weight or even as high as 1000 mg/kg of animal body weight may, however, be used.

The quantities referred to above of the compounds of general formula I may be administered on one or more occasions or divided into a number of smaller doses and administered over a period.

The valve of the compounds of formula F as anthelmintics has, for example, been demonstrated in the following tests:

A. Activity against roundworms in rats

Test 1 - Rats were infected with 100 Nippostrongylus brasiliensis larvae each, by the subcutaneous route. After 6 days, when the infection was patent, the rats were randomised and alloted to groups of 10 animals each, ready for treatment. One group was used for each dose level of the test compound and, in each experiment, one group was left untreated as a control. All the rats were killed for post-mortem worm counts 48 hours after treatment. The activity, expressed in terms of the percentage reduction in mean worm load of the treated group compared with the untreated group, is shown in Table I.

Test 2 — Rats were infected with 100 *Nippostrongylus brasiliensis* larvae each, by the subcutaneous route. After 24 hours the rats were randomised and allotted to groups of 5 animals each, ready for treatment. Doses of the test compound were then administered to each group by the oral, subcutaneous and intraperitoneal routes respectively, one group of 10 animals being left untreated as a control. All the rats were killed for post-mortem worm counts 6 days after dosing. The activities, expressed in terms of the percentage reductions in mean worm load of the treated groups or damage to the worms compared with the untreated control group, are given below in Table I.

TABLE I

| Test Compound | Test | Dose (mg/kg animal body weight) | Route of Administration | Percentage reduction in N.brasiliensis load or worm damage |
|---|---|---|---|---|
| 1-methoxycarbonyl-3-(2-aminophenyl)-thiourea | 1 | 1000 | oral | 99 and worm damage |
| 1-methoxycarbonyl-3-(2-amino-4-n-butylphenyl)thiourea | 1 | 500 | oral | 75 and worm damage |
| 1-methoxycarbonyl-3-(2-amino-4-isopropoxycarbonylaminophenyl)thiourea | 1 | 500 | oral | worm damage |
|  | 2 | 1000 | oral | 100 |
| 1-methoxycarbonyl-3-(2-acetamido-4-n-butylphenyl)-thiourea | 1 | 500 | oral | worm damage |
|  | 2 | 1000 | oral | 98 and worm damage |
| 1-methoxycarbonyl-3-)4-n-butyl-2-ethoxycarbonylaminophenyl)-thiourea | 1 | 500 | oral | 40 and worm damage |
| 1-methoxycarbonyl-3-(2-acetamido-5-n-butylphenyl)-thiourea | 1 | 1000 | oral | worm damage |
|  | 2 | 1000 | oral | 99 and worm damage |
| 1-methoxycarbonyl-3-(5-n-butyl-2-formamidophenyl)-thiourea | 1 | 1000 | oral | worm damage |
|  | 2 | 1000 | oral | 96 and worm damage |
| 1-methoxycarbonyl-3-(5-n-butyl-2-ethoxycarbonylaminophenyl)thiourea | 2 | 1000 | oral | 96 and worm damage |
| 1-ethoxycarbonyl-3-(2-acetamido-4-isopropoxycarbonylaminophenyl)thiourea | 2 | 1000 | oral | 62 |
| 1-ethoxycarbonyl-3-(2-amino-4-fluorophenyl)thiourea | 2 | 1000 | oral | 50 and worm damage |
| 1-(2-chloroethoxycarbonyl)-3-(2-aminophenyl)thiourea | 2 | 1000 | oral | 96 and worm damage |
| 1-methoxycarbonyl-3-(2-dimethylaminoacetamidophenyl)-thiourea hydrochloride | 1 | 1000 | oral | 91 and worm damage |
|  | 2 | 1000 | oral | 100 |
|  | 2 | 250 | intraperitoneal | 96 |
|  | 2 | 100 | intraperitoneal | 99 |
|  | 2 | 50 | intraperitoneal | 89 |
|  | 2 | 500 | subcutaneous | 99.5 |
|  | 2 | 250 | subcutaneous | 99.5 |
|  | 2 | 60 | subcutaneous | 89.8 |
| 1-methoxycarbonyl-3-(2-trimethylammoniumacetamidophenyl)thiourea iodide | 2 | 1000 | oral | worm damage |
| 1-ethoxycarbonyl-3-(2-dimethylaminoacetamidophenyl)-thiourea hydrochloride | 1 | 1000 | oral | 85 and worm damage |
|  | 2 | 1000 | oral | 98 and worm damage |
|  | 2 | 125 | intraperitoneal | 85 and worm damage |
|  | 2 | 100 | subcutaneous | 76 and worm damage |
| 1-ethoxycarbonyl-3-(2-trimethylammoniumacetamidophenyl)thiourea iodide | 2 | 1000 | oral | 60 and worm damage |
| 1-methoxycarbonyl-3-(2-amino-4-meth- | 1 | 1000 | oral | 100 |
|  | 2 | 1000 | oral | 100 |

TABLE I-continued

| Test Compound | Test | Dose (mg/kg animal body weight) | Route of Administration | Percentage reduction in N.brasiliensis load or worm damage |
|---|---|---|---|---|
| oxycarbonylamino-phenyl)thiourea | 2 | 500 | oral | 99 |
|  | 2 | 250 | oral | 99 |
| 1-(2-ethoxyethoxy-carbonyl)-3-(2-aminophenyl)thiourea | 2 | 1000 | oral | 90 and worm damage |
| 1-methoxycarbonyl-3-(2-dimethylamino-propionamidophenyl)-thiourea hydrochloride | 1 | 1000 | oral | 20 and worm damage |
|  | 2 | 1000 | oral | 98 and worm damage |
| 1-ethoxycarbonyl-3-[2-(N-benzyl-N-methylaminoacet-amido)phenyl]thiourea hydrochloride | 1 | 1000 | oral | 50 and worm damage |
|  | 2 | 1000 | oral | 99 and worm damage |
| 1-ethoxycarbonyl-3-(2-di-n-butyl-aminoacetamido-phenyl)thiourea hydrochloride | 2 | 1000 | oral | 97 and worm damage |
| 1-ethoxycarbonyl-3-[2-(N-methyl-N-butylaminoacet-amido)phenyl]thiourea hydrochloride | 1 | 1000 | oral | 86 and worm damage |
|  | 2 | 1000 | oral | 99 and worm damage |
| 1-ethoxycarbonyl-3-(5-n-butyl-2-dimethylaminoacet-amidophenyl)thiourea hydrochloride | 1 | 1000 | oral | 30 and worm damage |
|  | 2 | 1000 | oral | 88 and worm damage |
| 1-ethoxycarbonyl-3-(2-piperidino-acetamidophenyl)-thiourea hydrochloride | 1 | 1000 | oral | 85 and worm damage |
|  | 2 | 1000 | oral | 98 and worm damage |
| 1-ethoxycarbonyl-3-(2-dimethyl-aminoacetamido-5-isopropoxycarbon-ylaminophenyl)-thiourea hydrochloride | 1 | 1000 | oral | worm damage |
|  | 2 | 1000 | oral | 100 |
|  | 2 | 250 | sub-cutaneous | 60 and worm damage |
|  | 2 | 250 | intraper-itoneal | 50 and worm damage |
| 1-ethoxycarbonyl-3-(2-diethylamino-acetamidophenyl)-thiourea hydrochloride | 1 | 1000 | oral | 44 and worm damage |
|  | 2 | 1000 | oral | 100 |
|  | 2 | 250 | sub-cutaneous | 95 and worm damage |
|  | 2 | 250 | intraper-itoneal | 99 and worm damage |
| 1-ethoxycarbonyl-3-(2-morpholino-acetamidophenyl)-thiourea hydrochloride | 2 | 1000 | oral | 99 |
| 1-methoxycarbonyl-3-(2-amino-4-methylphenyl)thiourea | 2 | 1000 | oral | 97 and worm damage |
| 1-propargyloxy-carbonyl-3-(2-aminophenyl)thiourea | 1 | 1000 | oral | 76 and worm damage |
|  | 2 | 1000 | oral | 100 |
| 1-methoxycarbonyl-3-(2-amino-4-ethoxycarbonylamino-phenyl)thiourea | 2 | 1000 | oral | 99 |
| 1-ethoxycarbonyl-3-(2-dimethylamino-acetamido-5-methoxy-carbonylaminophenyl)-thiourea hydrochloride | 2 | 1000 | oral | 100 |
| 1-methoxycarbonyl-3-(4-acetyl-2-amino-phenyl)thiourea | 2 | 1000 | oral | 73 and worm damage |
| 1-ethoxycarbonyl-3-[2-(4-methyl-piperazin-1-yl-acetamido)phenyl]-thiourea dihydro-chloride | 1 | 1000 | oral | worm damage |
|  | 2 | 1000 | oral | 100 |
| 1-methoxycarbonyl-3-[2-(carboxy-acrylamido)phenyl]-thiourea | 2 | 1000 | oral | 99 |
| 1-ethoxycarbonyl- | 2 | 250 | sub- | 95 |

TABLE I-continued

| Test Compound | Test | Dose (mg/kg animal body weight) | Route of Administration | Percentage reduction in N.brasiliensis load or worm damage |
|---|---|---|---|---|
| 3-[2-(2,6-cis-dimethylmorpholino-acetamido)phenyl]-thiourea hydrochloride | 2 | 250 | cutaneous intraperitoneal | 93 |
| 1-ethoxycarbonyl-3-[2-(4-methyl-piperazin-1-yl-acetamido)phenyl]-thiourea dihydrochloride | 2 | 250 | subcutaneous | 93 |
|  | 2 | 250 | intraperitoneal | 98 |
| ± 1-ethoxycarbonyl-3-[2-(1-dimethylaminopropionamido)-phenyl]thiourea | 2 | 1000 | oral | 100 |
|  | 1 | 1000 | oral | 97 |
| 1-methoxycarbonyl-3-(2-aminophenyl)-thiourea nitrate | 2 | 1000 | oral | 99 |
|  | 1 | 1000 | oral | 99 |
| 1-methoxycarbonyl-3-(2-aminophenyl)-thiourea p-toluene-sulphonate | 2 | 1000 | oral | 99 |
|  | 1 | 1000 | oral | 98 |
| 1-methoxycarbonyl-3-(2-aminophenyl)-thiourea hydrochloride | 2 | 1000 | oral | 100 |
|  | 1 | 1000 | oral | 100 |

B. Activity against roundworms in mice

Mice were infected with approximately 100 Trichinella spiralis larvae each, by the oral route. The mice were randomised and allotted to two groups of 4 animals each. Doses of 1-methoxycarbonyl-3-(2-dimethylaminoacetamidophenyl)thiourea hydrochloride were then administered to one group by the subcutaneous route at 2 hours post infection and again at 24 hours post infection, one group of 4 animals being left untreated as a control. The doses given to the mice were 100 mg/kg animal body weight. All the mice were killed for postmortem examination 5 days after the second dose. The activity, expressed in terms of the percentage reduction in mean worm load of the treated group compared with the control group, was 95%.

C. Activity against roundworms in sheep a. Activity against Haemonchus contortus, Trichostrongylus axei and Trichostrongylus colubriformis in their 4th larval and adult stages in lambs i. 9 Worm-free lambs were each infected with H.contortus (approximately 9,000), T. axei (approximately 7,000) and T. colubriformis (approximately 12,000) infective larvae. After 7 days, 4 lambs were treated orally with 100 mg/kg animal body weight of the 2 test compounds, i.e. 2 lambs per compound, against the 4th larval stages of the worms. 23 Days after infection, all 9 lambs were killed for post-mortem worm counts and the burdens of each worm species in the 4 treated animals compared with those in the remaining 5 untreated control animals. These results are shown hereinafter in Table II.

ii. 20 Worm-free lambs were each infected with H. contortus (approximately 5,600), T. axei (approximately 9,300) and T. colubriformis (approximately 10,000) infective larvae. After 22 days, 16 lambs were treated orally with 15 mg/kg animal body weight of the 8 test compounds, i.e. 2 lambs per compound, against the mature adult stages of the worms. 27 Days after infection, all 20 lambs were killed for post-mortem worm counts and the burden of each worm species in the 16 treated animals compared with those in the remaining 4 untreated control animals. These results are shown hereinafter in Table III.

TABLE II

| | Mean percentage reduction in worm burdens | | |
|---|---|---|---|
| Compound | H.contortus | T.axei | T.colubriformis |
| 1-methoxycarbonyl-3-(2-amino-4-n-butyl-phenyl)thiourea | 100 | 99.5 | 100 |
| 1-methoxycarbonyl-3-(2-acetamido-4-n-butylphenyl)thiourea | 99.9 | 99.5 | 100 |

TABLE III

| | Mean percentage reduction in worm burdens | | |
|---|---|---|---|
| Compound | H.contortus | T.axei | T.colubriformis |
| 1-methoxycarbonyl-3-(2-acetamido-5-n-butyl-phenyl)thiourea | 82.1 | 98.2 | 95.0 |
| 1-methoxycarbonyl-3-(2-amino-4-isopropoxycarbonylaminophenyl)thiourea | 97.7 | 94.6 | 83.0 |
| 1-methoxycarbonyl-3-(5-n-butyl-2-ethoxycarbonyl-aminophenyl)thiourea | 79.6 | 78.6 | 40.1 |
| 1-methoxycarbonyl-3-(2-dimethylaminoacetamido-phenyl)thiourea hydrochloride | 60.0 | 78.0 | 43.4 |
| 1-methoxycarbonyl-3-(2-acetamido-4-n-butyl-phenyl)thiourea | 76.7 | 66.9 | 6.7 |
| 1-methoxycarbonyl-3-(4-n-butyl-2-formamido-phenyl)thiourea | 84.3 | 84.2 | 36.9 |
| 1-methoxycarbonyl-3-(2-cyclopropylcarbonamido-4-n-butylphenyl)thiourea | 58.4 | 57.6 | 27.1 |
| 1-methoxycarbonyl-3-(2-formamido-4-isopropoxycarbonylaminophenyl)- | 40.1 | 70.8 | 29.6 |

TABLE III-continued

| Compound | Mean percentage reduction in worm burdens | | |
|---|---|---|---|
| | H.contortus | T.axei | T.colubriformis |
| thiourea | | | | b. 8 Worm-free lambs were each infected with *H. contortus* (approximately 7,000) and *T. colubriformis* ((approximately 15,000) infective larvae. After 7 days, 2 lambs were treated by subcutaneous injection of an 18% w/v aqueous solution at 75 mg/kg animal body weight of the test compound against the 4th larval stages of the worms. 28 Days after infection, 2 lambs were similarly treated against the adult stages of the worms. 35 Days after infection all 8 lambs were killed for post-mortem worm counts and the burdens of each worm species in the 4 treated animals compared with those in the remaining 4 untreated animals.

| Compound | Stage | Mean percentage reduction in worm burdens | |
|---|---|---|---|
| | | H. contortus | T.colubriformis |
| 1-methoxy-carbonyl-3-(2-dimethyl-aminoacetamido-phenyl)thiourea hydrochloride | 4th larval | 87.1 | 99.9 |
| | adult | 95.3 | 99.7 | c. Effect on faecal egg output in naturally infected sheep (ewes)

Faecal material from sheep with naturally acquired strongyle infections was incubated for 7 days at 27° C. followed by identification of the infective larvae present. Amongst those species present were *O. circumcincta*, *H. contortus* and *Cooperia* spp.

Egg counts were carried out on individual samples of faeces taken from the animals two and one day previous to dosings.

Similar counts were carried out immediately after dosing and at intervals until 3 weeks after dosing, the animals having been randomised into comparable groups on the basis of the egg counts determined before dosing.

Egg counts were made using the McMaster technique. If a count by this technique was negative, a positive/negative egg flotation determination was made.

A group of 3 ewes was treated orally with 50 mg/kg animal body weight of test compound and further egg counts made at intervals for 3 weeks after treatment. The results are shown hereinafter in Table IV.

TABLE IV

| Compound | Mean faecal egg count/gm. faeces | | | | | | | | | | |
|---|---|---|---|---|---|---|---|---|---|---|---|
| | Days before treatment with drug | | Treatment day | Days after treatment with drug | | | | | | | |
| | 2 | 1 | | 1 | 4 | 6 | 8 | 11 | 15 | 18 | 20 | 22 |
| 1-methoxycarbonyl-3-(2-aminophenyl)-thiourea | 250 | 400-450 | 417-450 | 450 | 250 | 50 | 134 | 50-67 | 75 | 100 | 50 | 50 |

D. In vitro activity against roundworms

Compounds of formula I were tested at concentrations of 100 μg/ml, 10 μg/ml, 1 μg/ml and 0.1 μg/ml in small glass containers. If the compound was not soluble in water, a volatile organic medium, e.g. acetone, chloroform, ethanol or methanol was used. An amount of material appropriate for each final concentration was measured and placed in duplicate test containers and if an organic solvent was used it was allowed to evaporate completely.

*Nippostrongylus brasiliensis* eggs were recovered by saturated saline centrifugal flotation from the faeces of rats heavily infected with third stage larvae six days previously. They were washed several times in water and suspended in water in a suitable concentration. From 25-50 eggs were placed in each container and the final volume was made up by the addition of a very dilute aqueous suspension of mouse faeces which served as the growth medium.

The minimum inhibitory concentrations of each compound (M.I.C.), shown in the following Table V was the minimum concentration in μg/ml total liquid volume at which it inhibited or delayed hatching of eggs, or at which it killed, retarded growth or reduced activity of larvae during the 4 days after beginning the test.

TABLE V

| COMPOUND | M.I.C. (μg/ml) |
|---|---|
| 1-methoxycarbonyl-3-(2-aminophenyl)thiourea | 0.1 |
| 1-methoxycarbonyl-3-(2-amino-4-n-butylphenyl)-thiourea | 0.1 |
| 1-methoxycarbonyl-3-(2-amino-4-isopropoxy-carbonylaminophenyl)thiourea | 100.0 |
| 1-methoxycarbonyl-3-(2-acetamido-4-n-butyl-phenyl)thiourea | 0.1 |
| 1-methoxycarbonyl-3-(4-n-butyl-2-formamido-phenyl)thiourea | 0.1 |
| 1-methoxycarbonyl-3-(2-cyclopropylcarbonamido-4-n-butylphenyl)thiourea | 0.1 |
| 1-methoxycarbonyl-3-(2-cyclopropylcarbonamido-5-n-butylphenyl)thiourea | 0.1 |
| 1-methoxycarbonyl-3-(4-n-butyl-2-ethoxycarbonyl-aminophenyl)thiourea | 0.1 |
| 1-methoxycarbonyl-3-(2-acetamido-5-n-butylphenyl)- | |

TABLE V-continued

| COMPOUND | M.I.C. (μg/ml) |
|---|---|
| thiourea | 0.1 |
| 1-methoxycarbonyl-3-(5-n-butyl-2-formamidophenyl)-thiourea | 0.1 |
| 1-methoxycarbonyl-3-(5-n-butyl-2-ethoxycarbonylaminophenyl)thiourea | 10.0 |
| 1-ethoxycarbonyl-3-(2-amino-4-fluorophenyl)-thiourea | 1.0 |
| 1-ethoxycarbonyl-3-(2-amino-4-n-butylphenyl)-thiourea | 1.0 |
| 1-n-butoxycarbonyl-3-(2-aminophenyl)thiourea | 1.0 |
| 1-(2-chloroethoxycarbonyl)-3-(2-aminophenyl)-thiourea | 100.0 |
| 1-methoxycarbonyl-3-(2-dimethylaminoacetamidophenyl)thiourea hydrochloride | 1.0 |
| 1-methoxycarbonyl-3-(2-trimethylammoniumacetamidophenyl)thiourea iodide | 1.0 |
| 1-ethoxycarbonyl-3-(2-dimethylaminoacetamidophenyl)thiourea hydrochloride | 0.1 |
| 1-ethoxycarbonyl-3-(2-trimethylammoniumacetamidophenyl)thiourea iodide | 0.1 |
| 1-methoxycarbonyl-3-(2-amino-4-methoxycarbonylaminophenyl)thiourea | 100.0 |
| 1-methoxycarbonyl-3-(2-dimethylaminopropionamidophenyl)thiourea hydrochloride | 1.0 |
| 1-ethoxycarbonyl-3-(2-N-benzyl-N-methylaminoacetamidophenyl)thiourea hydrochloride | 0.1 |
| 1-ethoxycarbonyl-3-(2-di-n-butylaminoacetamidophenyl)thiourea hydrochloride | 0.1 |
| 1-ethoxycarbonyl-3-(2-N-methyl-N-n-butylaminoacetamidophenyl)thiourea hydrochloride | 1.0 |
| 1-ethoxycarbonyl-3-(5-n-butyl-2-dimethylaminoacetamidophenyl)thiourea hydrochloride | 0.1 |
| 1-ethoxycarbonyl-3-(2-piperidinoacetamidophenyl)-thiourea hydrochloride | 1.0 |
| 1-ethoxycarbonyl-3-(2-dimethylaminoacetamido-5-isopropoxycarbonylaminophenyl)thiourea hydrochloride | 100.0 |
| 1-ethoxycarbonyl-3-(2-diethylaminoacetamidophenyl)thiourea hydrochloride | 0.1 |
| 1-ethoxycarbonyl-3-(2-morpholinoacetamidophenyl)-thiourea hydrochloride | 0.1 |
| 1-methoxycarbonyl-3-(2-amino-4-methylphenyl)-thiourea | 100.0 |
| 1-propargyloxycarbonyl-3-(2-aminophenyl)thiourea | 1.0 |
| 1-methoxycarbonyl-3-(2-amino-4-ethoxycarbonylaminophenyl)thiourea | 10.0 |
| 1-ethoxycarbonyl-3-(2-trimethylammoniumacetamidophenyl)thiourea chloride | 0.1 |
| 1-ethoxycarbonyl-3-(2-amino-4-chlorophenyl)-thiourea | 10.0 |
| 1-ethoxycarbonyl-3-[2-(4-methylpiperazin-1-yl-acetamido)phenyl]thiourea dihydrochloride | 0.1 |
| 1-methoxycarbonyl-3-[2-(3-carboxyacrylamido)-phenyl]thiourea | 1.0 |
| 1-ethoxycarbonyl-3-[2-(2,6-cis-dimethylmorpholinoacetamido)phenyl]thiourea hydrochloride | 0.1 |

The compounds of general formula I also possess valuable anti-viral activity, for example against the myxovirus A₂/Hong Kong/5/68 which causes influenza in man. The quantities of the compounds of formula I administered in the treatment of viral infections will vary with the species of animal treated, the nature and severity of the infection, the length of treatment and the method of administration. In general, the compounds are effective in treating viral infections, more particularly infections of virus A₂/Hong Kong/5/68, when administered orally at dosages between 50 and 250 mg/kg of animal body weight. The quantities may be administered on one or more occasions or divided into a number of smaller doses and administered over a period.

The anti-viral activity of the compounds of general formula I has, for example, been demonstrated in the following test:

Groups of five mice, each weighing approximately 20 g., were dosed with the test compound at a rate of 250 mg/kg animal body weight by oral administration. Three hours later each animal was infected by intranasal inoculation with 0.02 ml. of a $10^{-1}$ dilution of a suspension of lung tissue, disintegrated by ultrasonic vibration, from mice infected with influenza virus type A₂/Hong Kong/5/68. One hour after infection, the animals were again dosed orally with the test compound at the same rate of administration. Twenty four hours after infection, the mice were killed, the lungs removed and those from the five animals which had received the same test compound were pooled and disintegrated by ultrasonic vibration in phosphate-buffered saline to give a 10% w/v suspension. After incubation for one hour at 37° C. and centrifugation, the supernatant fluid was removed and serially diluted from a concentration of 1/2 to 1/8192. The viral content was then determined by the addition of a 0.5% w/v suspension of chicken blood red cells to determine the greatest dilution of supernatant fluid which produced agglutination of the chicken blood red cells (the haemagglutinin titre) and compared with the corresponding haemagglutinin titre obtained from similarly-infected, untreated, control animals.

The results obtained are set out in the following Table VI.

TABLE VI

| Test Compound | Haemagglutinin titre-treated animals | Haemagglutinin titre-control animals |
| --- | --- | --- |
| 1-ethoxycarbonyl-3-[2-(N-methyl-N-n-butylamino-acetamido)phenyl]thiourea hydrochloride | 1/4 | 1/256 |
| 1-methoxycarbonyl-3-(2-acetamido-5-isopropoxy-carbonylaminophenyl)-thiourea | 1/128 | 1/4096 |
| 1-methoxycarbonyl-3-(2-acetamido-4-isopropoxy-carbonylaminophenyl)-thiourea | 1/256 | 1/4096 |
| 1-ethoxycarbonyl-3-(2-amino-4-fluorophenyl)-thiourea | 1/32 | 1/2048 |
| 1-(2-chloroethoxycarbonyl)-3-(2-aminophenyl)thiourea | 1/32 | 1/2048 |
| 1-methoxycarbonyl-3-)2-trimethylammoniumacet-amidophenyl)thiourea iodide | 1/256 | 1/2048 |
| 1-methoxycarbonyl-3-(2-amino-4-methoxycarbonyl-aminophenyl)thiourea | 1/512 | 1/4096 |
| 1-methoxycarbonyl-3-(2-cyclopropylcarbonamido-5-n-butylphenyl)thiourea | 1/128 | 1/2048 |
| 1-methoxycarbonyl-3-(5-n-butyl-2-formamido-phenyl)thiourea | 1/32 | 1/256 |
| 1-methoxycarbonyl-3-(5-n-butyl-2-ethoxycarbonyl-aminophenyl)thiourea | 1/64 | 1/512 |
| 1-ethoxycarbonyl-3-(2-acetamido-5-isopropoxy-carbonylaminophenyl)-thiourea | 1/256 | 1/2048 |
| 1-methoxycarbonyl-3-(2-formamido-5-isopropoxy-carbonylaminophenyl)-thiourea | 1/256 | 1/2048 |

The compounds of general formula I are conveniently administered as anthelmintics and anti-viral agents in the form of compositions in a unit dosage form, and the present invention includes within its scope therapeutically-useful, more especially veterinary, compositions which comprise, as active ingredient, at least one benzene derivative of formula I in association with a significant amount of a pharmaceutically-acceptable carrier or coating. The invention includes especially such compositions made up for oral administration, for example a tablet, pill, capsule or bolus, or more particularly, a paste, gel or drench.

Solid compositions for oral administration include compressed tablets, pills, boluses and granules, which may optionally be coated with a pharmaceutically acceptable alkali-stable or acid-stable material (e.g. an enteric coating) and dispersible powders. In such solid compositions one or more of the active compounds is or are admixed with at least one inert diluent such as potato starch, alginic acid, sucrose, lactose, or a resin. The compositions may also comprise, as is normal practice, additional substances other than inert diluents, e.g. lubricating agents such as magnesium stearate. Semi-solid compositions for oral administration include pastes and gels containing the active substance and a suitable inert diluent such as polyethylene glycol (6000). Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise compatible adjuvants such as wetting, suspending and emulsifying agents and stabilising, thickening, perfuming, sweetening and flavouring agents. The compositions according to the invention for oral administration also include capsules of absorbable material such as gelatin containing one or more of the active substances with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents. They may be sterilised, for example, by filtration through a bacteria-retaining filter, by incorporation in the compositions of sterilising agents, or by heating. They may also be manufactured in the form of sterile solid compositions, which can be dissolved in sterile water or some other sterile injectable medium immediately before use.

The percentage of the benzene derivatives of formula I in the above compositions may be varied, it being necessary that it should constitute a proportion such that a suitable dosage for the therapeutic effect desired shall be obtained. In general, compositions containing from about 5 to about 90% by weight of active ingredient are satisfactory.

For therapeutic purposes, particularly when continuous administration over a period is desired, the compounds of general formula I may be administered dispersed in, or mixed with, animal feedstuffs, drinking water and other liquids normally consumed by the animals, or in compositions containing the benzene derivatives dispersed in or mixed with any other suitable inert physiologically innocuous carrier or diluent which is orally administrable. By the term 'inert physiologically innocuous carrier or diluent' is meant a carrier or diluent which is substantially non-reactive with the active ingredient and is not harmful to the animals on oral administration. Such compositions may be administered in the form of powders, pellets, solutions, suspensions and emulsions, to the animals to supply the desired dosage of the benzene derivatives or used as concentrates or supplements to be diluted with additional carrier, feed-stuff, drinking water or other liquids normally consumed by the animals, before administration. Suitable inert physiologically innocuous carriers or diluents include wheat flour or meal, maize gluten, lactose, glucose, sucrose, talc, kaolin, calcium phosphate, potassium sulphate and diatomaceous earths such as keiselguhr. Concentrates or supplements intended for incorporation into drinking water or other liquids normally consumed by the animals to give solutions, emulsions or stable suspensions, may also comprise the active ingredient in association with a surface-active wetting, dispersing or emulsifying agent such as Teepol, polyoxyethylene(20)sorbitan mono-oleate or the condensation product of β-naphthalenesulphonic acid with formaldehyde, with or without a physiologically innocuous, preferably water-soluble, carrier or diluent, for example, sucrose, glucose or an inorganic salt such as potassium sulphate, or concentrates or supplements in the form of stable dispersions or solutions obtained by mixing the aforesaid concentrates or supplements with water or some other suitable physiologically innocuous inert liquid carrier or diluent, or mixtures thereof.

The compositions described above may be prepared by mixing the benzene derivatives of formula I with the inert physiologically innocuous carriers or diluents in any manner known to the art. Solid compositions are conveniently prepared by intimately mixing or dispersing the benzene derivatives uniformly throughout the feedstuffs or other solid carrier or diluent by methods such as grinding, stirring, milling or tumbling or by dissolving the benzene derivatives in a solvent, e.g. water or a suitable organic solvent, dispersing the solution so obtained in the feedstuff or other solid carrier or diluent and removing the solvent by any means known to the art. Medicated feedstuffs may also be prepared by mixing in concentrates or supplements containing higher concentrates of active ingredient to give feedstuffs throughout which the benzene derivatives are uniformly distributed at the desired concentration. The desired concentration of active ingredient in the compositions of the present invention is obtained by the selection of an appropriate ratio of the benzene derivatives to carrier or diluent.

Medicated feedstuffs will normally contain between 0.001 and 3% by weight of the benzene derivatives of formula I to give the required dosage. Concentrates and supplements will normally contain between 5 and 90%, preferably 5 to 50%, by weight of the benzene derivatives being, if desired, suitably diluted as hereinbefore described to give the required dosage.

Medicated animal feedstuffs, drinking water and other liquids normally consumed by the animals and compositions containing the benzene derivatives of formula I dispersed in, or admixed with, any other suitable inert carrier or diluent, as hereinbefore described, including concentrates or supplements, form further features of the present invention.

Compositions according to the present invention may also contain bacteriostats, bactericidal agents, sporicidal agents and pharmaceutically-acceptable colouring agents. The compositions may also contain, if desired, auxiliary therapeutic agents, for example fluke drugs such as 4-cyano-2-iodo-6-nitrophenol, hexachloroethane, carbon tetrachloride, 3,3',5,5',6,6'-hexachloro-2,2'-dihydroxydiphenylmethane, 2,2'-dihydroxy-3,3',5,5',6-pentachlorobenzanilide, 2,2'-dihydroxy-3,3'-dinitro-5,5'-dichlorodiphenyl or 2-acetoxy-4'-chloro-3,5-diiodobenzanilide, 2-(4-thiazolyl)benzimidazole, 5(6)-isopropoxycarbonylamino-2(4-thiazolyl)benzimidazole, methyl 5(6)-butyl-2- benzimidazolecarbamate, methyl 5(6)-benzoyl-2-benzimidazolecarbamate, 6-phenyl-2,3,5,6-tetrahydroimidazo[2,1,-b]-thiazole, trans-1,4,5,6-tetrahydro-1-methyl-2-(2-thien-2'-ylvinyl)pyrimidine, phenothiazine, cyanacethydrazide, piperazine and its salts such as piperazine adipate, 1-diethylcarbamoyl-4-methylpiperazine, tetrachloroethylene, 4,4'-dichloro-2,2'-dihydroxydiphenylmethane, N-(2-chloro-4-nitrophenyl)-5-chlorosalicylamide, N,N-dibutyl-4-hexyloxynaphthamidine, trans-1,4-bis-(2-isothiocyanatoethyl)cyclohexane and 1-styrylpyridinium salts, e.g. the bromide, embonate, amsonate or isethionate.

Compounds of general formula I may be prepared by the suitable adaptation of known methods, for example:

1. by the reaction of equimolecular quantities of an isothiocyanate of the general formula:

SCNCO₂R IV (wherein R is as hereinbefore defined) and an amine of the general formula:

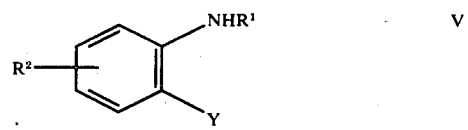

V wherein R¹, R² and Y are as hereinbefore defined, with the proviso that when R¹ in the compound of formula V represents a methyl group Y preferably represents a monomethylamino group, and that when R¹ in the compound of formula V represents a hydrogen atom Y preferably represents a primary amino group. The reaction may be carried out in the presence of an inert solvent, for example a lower alkanone, e.g. acetone or methylethyl ketone, a lower alkanol, e.g. methanol or ethanol, dioxan, acetonitrile or an aromatic hydrocarbon, e.g. toluene, at a temperature between 0° and 150° C. and preferably at between 10° and 60° C.

As will be readily apparent to those skilled in the art, when R² in the compounds of formula V is other than a hydrogen atom, the reaction may give rise to a mixture of compounds of formula I which are isomeric in respect of the positional relationship of the substituent R² relative to Y and the grouping —n(R¹)CSNHCOOR. These mixtures may be separated into their component compounds of formula I by known methods, for example chromatography or fractional crystallisation but, accordingly, when Y in the compound of formula V represents a primary amino or methylamino group, $R^2$ is preferably hydrogen.

CThe isothiocyanates of general formula IV may be prepared by the reaction of an ester of the general formula:

$$X^1CO_2R \qquad \text{VI}$$

(wherein R is as hereinbefore defined and $X^1$ is a bromine, iodine or, preferably, chlorine atom) and a thiocyanate of the general formula:

$$(NCS)_qM \qquad \text{VII}$$

(wherein M is a metal, preferably an alkali metal or an alkaline earth metal atom and q is the valency of that metal). The reaction may be carried out in the presence of an inert organic solvent, for example a lower alkanone, e.g. acetone, or acetonitrile, at a temperature between 0° and 100° C., and preferably between 20° and 50° C.

The preparation of compounds of formula IV may be effected in situ for subsequent reaction with compounds of formula V or, if desired, the compounds of formula IV may be isolated by known methods prior to reaction with compounds of formula V.

2. by the reduction of compounds of the general formula:

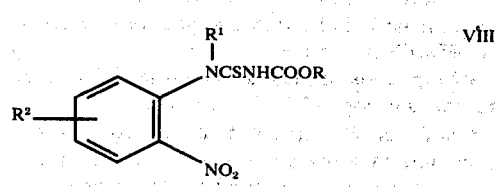

(wherein R, $R^1$ and $R^2$ are as hereinbefore defined) by known methods for the reduction of an aromatic nitro group in compounds containing sulphur under neutral or acidic conditions, for example with ferrous chloride, ferrous hydroxide, stannous chloride, reduced iron powder or iron pin dust, if desired in the presence of an inorganic acid, e.g. hydrochloric acid, or an alkanoic acid containing 1 to 4 carbon atoms, which may optionally be substituted by a cycloalkyl group containing 3 to 6 carbon atoms, or an acid anhydride of such an alkanoic acid, to give a compound of general formula I wherein Y represents a primary amino group, or a group —$NHR^4$ in which $R^4$ represents a straight- or branched-chain alkanoyl group containing 1 to 4 carbon atoms which may optionally be substituted by a cycloalkyl group containing from 3 to 6 carbon atoms. Reduction may be carried out in an aqueous-organic inert solvent medium, for example an aqueous lower alkanol, e.g. aqueous methanol, or aqueous ethanol, or an aqueous lower alkanone, e.g. aqueous acetone, at a temperature between 20° C. and the reflux temperature of the reaction mixture. Reduction with reduced iron powder may, if desired, be carried out in the presence of an inorganic chloride, for example ammonium chloride, magnesium chloride or ferric chloride.

3. by the reaction of an amine of the general formula:

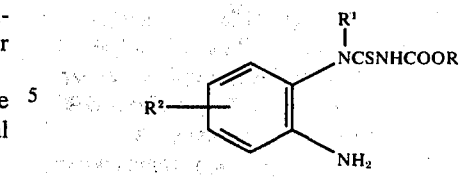

(wherein R, $R^1$ and $R^2$ are as hereinbefore defined) with a compound of the general formula:

$$X^1COR^8 \qquad \text{X}$$

(wherein $X^1$ is as hereinbefore defined and $R^8$ represents a straight- or branched-chain alkyl group containing 1 to 3 carbon atoms, which may optionally be substituted by a cycloalkyl group containing from 3 to 6 carbon atoms, a cycloalkyl group containing from 3 to 6 carbon atoms or a straight- or branched-chain alkoxy group containing 1 to 3 carbon atoms) or with formic acid to give a compound of general formula I wherein $R^4$ represents an alkanoyl, cycloalkylcarbonyl or alkoxycarbonyl group and $R^3$ represents a hydrogen atom. The reaction is preferably carried out in an inert organic solvent, for example a lower alkanone, e.g. acetone, or an aromatic hydrocarbon, e.g. toluene, at a temperature between 0° C. and the reflux temperature of the reaction mixture and preferably at 30° C. to 110° C. When formic acid is used as reactant, it may also serve as the reaction medium.

4. by reaction of an anhydride of the general formula:

(wherein A is as hereinbefore described) with a compound of general formula IX (wherein R, $R^1$ and $R^2$ are as hereinbefore defined) to give a compound of general formula I wherein Y represents a group —$NHR^4$ in which $R^4$ represents a group —COACOOH, A being as hereinbefore defined. The reaction is preferably carried out in an inert organic solvent, for example a lower alkanol, e.g. methanol or ethanol, at a temperature between 20° and 110° C., and preferably at the reflux temperature of the reaction mixture.

5. by reaction of a compound of the general formula:

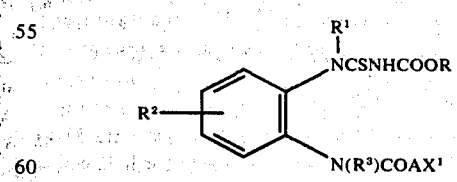

(wherein R, $R^1$, $R^2$, $R^3$, A and $X^1$ are as hereinbefore defined) with a. a compound of the general formula:

$$NHR^6R^7 \qquad \text{XIII}$$

(wherein $R^6$ and $R^7$ are as hereinbefore defined), an excess of which may be employed as an acid-binding agent, to give a compound of formula I wherein Y represents a group —NR³R⁴ wherein R³ is as hereinbefore defined and R⁴ represents a group —COAZ (wherein A is as hereinbefore defined and Z is a group of formula II, wherein R⁵ is a hydrogen atom, R⁶ and R⁷ are as hereinbefore defined and the anion X ⁻ is a halide ion derived from the halogen atom represented by X¹ in the compound of general formula XII, or of formula III, wherein R⁶ and R⁷ are as hereinbefore defined), or b. A compound of the general formula:

NR⁵R⁶R⁷  XIV (wherein R⁶ and R⁷ are as hereinbefore defined, and R⁵ represents a straight- or branched-chain alkyl group containing not more than 4 carbon atoms) to give a compound of formula I, wherein Y represents a group —NR³R⁴ wherein R³ is as hereinbefore defined and R⁴ represents a group —COAZ, in which A is as hereinbefore defined and Z is a group of formula II wherein R⁵ is a straight- or branched-chain alkyl group containing not more than 4 carbon atoms, R⁶ and R⁷ are as hereinbefore defined and the anion X ⁻ is a halide ion derived from the halogen atom represented by X¹ in the compound of general formula XII.

The reaction between the compound of general formula XII and the compound of general formula XIII may be carried out in an inert organic solvent, for example a lower alkanol, e.g. ethanol, or an aromatic hydrocarbon, e.g. benzene, at a temperature between 20° C. and 100° C., and preferably at the reflux temperature of the reaction mixture. The reaction between the compound of general formula XII and the compound of general formula XIV may be carried out in an inert organic solvent, for example ethyl acetate or diethyl ether, at a temperature between 20° C. and 80° C., and preferably at the reflux temperature of the reaction mixture.

6. by reaction of a compound of general formula I, wherein R, R¹ and R² are as hereinbefore defined and Y represents a group —N(R³)COANR⁶R⁷ (wherein R³, R⁶, R⁷ and A are as hereinbefore defined) with a compound of the general formula:

R⁵X²  XV (wherein R⁵ represents a hydrogen atom or a straight- or branched-chain alkyl group containing not more than 4 carbon atoms and X² is an atom or group corresponding to the anion X ⁻) to give compounds of formula I wherein Y represents a group —NR³R⁴ wherein R³ is as hereinbefore defined and R⁴ represents a group —COAZ, in which A is as hereinbefore defined and Z is a group of formula II, wherein R⁵ is a hydrogen atom or a straight- or branched-chain alkyl group containing not more than 4 carbon atoms, R⁶ and R⁷ are as hereinbefore defined and the anion X ⁻ is derived from the atom or group represented by the symbol X² in the compound of general formula XV. The reaction is preferably carried out in an inert organic solvent, for example ethanol, ethyl acetate or diethyl ether, at a temperature between 10° C. and 40° C.

Compounds of general formula V, wherein R² and Y are as hereinbefore defined and R¹ represents a hydrogen atom, may be prepared by the reduction of compounds of the general formula:

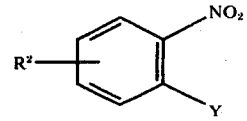

XVI (wherein R² and Y are as hereinbefore defined) by known methods for the reduction of aromatic nitro groups, for example by hydrogenation in the presence of a hydrogenation catalyst, e.g. platinum, or by the use of ferrous chloride and reduced iron powder.

Compounds of general formula XVI wherein Y represents a group —NR³R⁴ (wherein R³ is as hereinbefore defined and R⁴ represents an alkanoyl or alkoxycarbonyl group as hereinbefore defined) may be prepared by the reaction of a compound of the general formula:

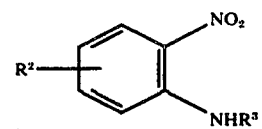

XVII (wherein R² and R³ are as hereinbefore defined) with a compound of general formula X (wherein X¹ and R⁸ are as hereinbefore defined) or with formic acid. The reaction may be carried out under the conditions hereinbefore described for the preparation of compounds of general formula I by the reaction of compounds of general formula IX with compounds of general formula X or with formic acid.

Compounds of general formula XVI wherein Y represents a group —NR³R⁴ (wherein R³ is as hereinbefore defined and R⁴ represents a hydrogen atom) may be prepared by known methods for the preparaion of o-nitroanilines and N-methyl-o-nitroanilines.

Compounds of general formula XVI, wherein Y represents a group —N(R³)COAZ (wherein R³, A and Z are as hereinbefore defined, may be prepared by the reaction of a compound of the general formula:

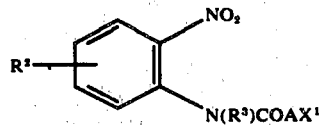

XVIII (wherein R², R³, A and X¹ are as hereinbefore defined) with a. a compound of general formula XIII (wherein R⁶ and R⁷ are as hereinbefore defined), an excess of which may be employed as an acid-binding agent, under the conditions hereinbefore described for the reaction of compounds of general formula XII with compounds of general formula XIII to give compounds of general formula XVI wherein Y represents a group —N(R³)COAZ (wherein R³ and A are as hereinbefore defined, and Z is a group of formula II wherein R⁵ is a hydrogen atom, R⁶ and R⁷ are as hereinbefore defined and the anion X⁻ is a halide ion derived from the halogen atom represented by X¹ in the compound of general formula XVIII, or of formula III wherein R⁶ and R⁷ are as hereinbefore defined), or b. a compound of general formula XI^V (wherein R⁶ and R⁷ are as hereinbefore defined, and R⁵ represents a straight- or branched-chain alkyl group containing not more than 4 carbon atoms) under the conditions hereinbefore described for the reaction of compounds of general formula XII with compounds of general formula XI$^V$ to give compounds of general formula XVI wherein Y represents a group —N(R$^3$)COAZ (wherein R$^3$ and A are as hereinbefore defined, and Z is a group of formula II wherein R$^5$ is a straight- or branched-chain alkyl group containing not more than 4 carbon atoms, R$^6$ and R$^7$ are as hereinbefore defined and the anion X$^-$ is a halide ion derived from the halogen atom represented by X$^1$ in the compound of general formula XVIII.

Compounds of general formula XVIII may be prepared by the reaction of a compound of general formula XVII (wherein R$^2$ and R$^3$ are as hereinbefore defined) with a compound of the general formula:

$$X^1COAX^1 \qquad XIX$$

wherein A and X$^1$ are as hereinbefore defined. The reaction is preferably carried out in an inert organic solvent, for example a lower alkanone, e.g. acetone, or an aromatic hydrocarbon, e.g. toluene, at a temperature between 0° and 100° C.

Compounds of general formula XVI wherein Y represents a group —N(R$^3$)COAZ (wherein R$^3$ and A are as hereinbefore defined and Z represents a group of general formula II wherein R$^5$, R$^6$, R$^7$ and X$^-$ are as hereinbefore defined) may be prepared by the reaction of a compound of general formula XVI wherein Y represents a group —N(R$^3$)COAZ (wherein R$^3$ and A are as hereinbefore defined and Z represents a group —NR$^6$R$^7$ in which R$^6$ and R$^7$ are as hereinbefore defined) with a compound of general formula XV, wherein R$^5$ and X$^2$ are as hereinbefore defined. The reaction may be carried out as hereinbefore described for the reaction of compounds of general formula XV with compounds of general formula I, wherein R, R$^1$ and R$^2$ are as hereinbefore defined and Y represents a group —N(R$^3$)COANR$^6$R$^7$ (wherein R$^3$, R$^6$, R$^7$ and A are as hereinbefore defined).

Compounds of general formula V, wherein R$^2$ is as hereinbefore defined, R$^1$ represents a methyl group and Y represents a group —N(CH$_3$)COAZ (wherein A and Z are as hereinbefore defined), may be prepared by the reaction of a compound of the general formula:

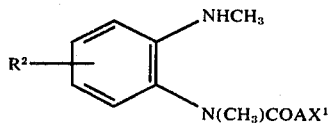

XX (wherein R$^2$, A and X$^1$ are as hereinbefore defined) with
a. a compound of general formula XIII (wherein R$^6$ and R$^7$ are as hereinbefore defined), an excess of which may be employed as an acid-binding agent, under the conditions hereinbefore described for the reaction of compounds of general formula XII with compounds of general formula XIII to give compounds of general formula V wherein R$^2$ is as hereinbefore defined, R$^1$ represents a methyl group and Y represents a group —N(CH$_3$)COAZ (wherein A is as hereinbefore defined and Z is a group of formula II wherein R$^5$ is a hydrogen atom, R$^6$ and R$^7$ are as hereinbefore defined and the anion X$^-$ is a halide ion derived from the halogen atom represented by X$^1$ in the compound of general formula XX, or of formula III wherein R$^6$ and R$^7$ are as hereinbefore defined), or b. a compound of general formula XIV (wherein R$^6$ and R$^7$ are as hereinbefore defined and R$^5$ represents a straight- or branched-chain alkyl group containing not more than 4 carbon atoms) under the conditions hereinbefore described for the reaction of compounds of general formula XII with compounds of general formula XIV to give compounds of general formula V wherein Y represents a group —N(R$^3$)—COAZ (wherein R$^3$ and A are as hereinbefore defined, and Z is a group of formula II wherein R$^5$ is a straight- or branched-chain alkyl group containing not more than 4 carbon atoms, R$^6$ and R$^7$ are as hereinbefore defined and the anion X$^-$ is a halide ion derived from the halogen atom represented by X$^1$ in the compound of general formula XX).

Compounds of general formula XX may be prepared by reaction of the appropriate N,N$^1$-dimethyl-o-phenylene-diamine with one molecular equivalent of a compound of general formula XIX (wherein X$^1$ is as hereinbefore defined) under the conditions hereinbefore described for the reaction of compounds of general formula XVII with compounds of general formula XIX.

Compounds of general formula V, wherein Y represents a group —N(R$^3$)COAZ (wherein R$^3$ and A are as hereinbefore defined and Z represents a group of general formula II wherein R$^5$, R$^6$, and R$^7$ and X$^-$ are as hereinbefore defined), may be prepared by the reaction of a compound of general formula V wherein Y represents a group —N(R$^3$)COAZ (wherein R$^3$ and A are as hereinbefore defined and Z represents a group —NR$^6$R$^7$ wherein R$^6$ and R$^7$ are as hereinbefore defined) with a compound of general formula XV wherein R$^5$ and X$^2$ are as hereinbefore defined. The reaction may be carried out under the conditions hereinbefore described for the reaction of compounds of general formula XV with compounds of general formula I wherein R, R$^1$ and R$^2$ are as hereinbefore defined and Y represents a group —N(R$^3$)COANR$^6$R$^7$ (wherein R$^3$, R$^6$, R$^7$ and A are as herinbefore defined).

Compounds of general formula V, wherein R$^2$ is as hereinbefore defined, R$^1$ represents a hydrogen atom and Y represents a group —N(R$^3$)COAZ (wherein R$^3$, A and Z are as hereinbefore defined), may be prepared from compounds of the general formula:

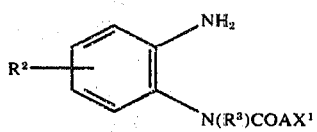

XXI (wherein R$^2$, R$^3$, A and X$^1$ are as hereinbefore defined) by the application of processes hereinbefore described for the preparation of compounds of general formula I from compounds of general formula XII.

Compounds of general formula XXI may be prepared by the reduction of compounds of general formula XVIII (wherein R$^2$, R$^3$, A and X$^1$ are as hereinbefore defined) by known methods for the reduction of aromatic nitro groups, for example as hereinbefore described for the reduction of compounds of general formula XVII, wherein R$^2$ and Y are as hereinbefore defined.

Compounds of general formula XII, wherein R, R$^1$, R$^2$, R$^3$, A and X$^1$ are as hereinbefore defined, may be obtained by the reaction of a compound of general formula I wherein R, R¹ and R² are as hereinbefore defined and Y represents a group —NHR³, R³ being as hereinbefore defined, with a compound of general formula XIX, wherein X¹ is as hereinbefore defined. The reaction may be carried out under the conditions hereinbefore described for the reaction of compounds of general formula XVII with compounds of general formula XIX.

Compounds of general formula XII, wherein R, R², R³, A and X¹ are as hereinbefore defined and R¹ represents a hydrogen atom, may alternatively be prepared by the reaction of a compound of general formula XXI (wherein R², R³, A and X¹ are as hereinbefore defined) with an isothiocyanate of general formula IV, wherein R is as hereinbefore defined. The reaction may be carried out under the conditions hereinbefore described for the reaction of compounds of general formula V to give compounds of general formula I.

Acid addition salts of those compounds of general formula I wherein Y represents a primary amino group may be prepared by known method, for example by reaction of the base with an acid e.g. hydrochloric, nitric, methanesulphonic or toluene-p-sulphonic acid, in an appropriate solvent medium, e.g. an ether such as diethyl ether.

By the term 'known methods' as used in the present specification is meant methods heretofore used or described in the chemical literature.

For example, compounds hereinbefore described may be prepared by the following Procedures.

PROCEDURE A

Potassium thiocyanate (24.2 g; 0.25 mole), methyl chloroformate (23.6 g; 0.25 mole) and dry acetone (150 ml) were mixed with stirring at laboratory temperature. The temperature of the reaction mixture rose spontaneously to 51° C., and stirring was continued for two hours at 45° C. to 51° C. The reaction mixture was then cooled in an ice-bath to a temperature of 15° C., and o-phenylenediamine (27.0 g; 0.25 mole) was then added in portions, with stirring, over a period of fifteen minutes, the temperature of the stirred reaction mixture being maintained between 15° and 20° C. during the addition. When the addition was complete, the reaction mixture was stirred at laboratory temperature for eighteen hours and then filtered. The solid residue was washed with water and dried in a vacuum dessicator to give a crude product (5.0 g), m.p. 189° C. (with decomposition).

The crude product was recrystallised from dry ethanol (40 ml) to give 1-methoxycarbonyl-3-(2-aminophenyl)thiourea (3.5 g), m.p. 189°–190° C. (with decomposition).

PROCEDURE B

Methyl chloroformate (23.6 g; 0.25 mole) was added dropwise to a stirred suspension of potassium thiocyanate (24.2 g; 0.25 mole) in dry acetonitrile (100 ml). The temperature of the reaction mixture rose spontaneously to 50° C. and stirring was continued for two hours at 45° C. to 50° C. The reaction mixture was then filtered and the clear filtrate was added dropwise during fifteen minutes to a suspension of o-phenylenediamine (27 g; 0.25 mole) in dry acetonitrile (20 ml), the temperature during the addition being maintained between 15° C. and 20° C. by external cooling. When the addition was complete, the reaction mixture was stirred at laboratory temperature for two hours, filtered, and the crude solid product was crystallised from ethanol to give colourless needles of 1-methoxycarbonyl-3-(2-aminophenyl)-thiourea (15.3 g), m.p. 183.5°–184.5° C. (with decomposition).

Concentrated hydrochloric acid (3 ml) was added dropwise to a stirred suspension of 1-methoxycarbonyl-3-(2-aminophenyl)thiourea in dry dioxan (75 ml), the temperature of the reaction mixture being maintained at 20°–25° C. during the addition by slight external cooling. The clear solution obtained was stirred for a further 30 minutes at 25° C. during which time a solid separated. This was filtered off, washed with acetone and recrystallised from ethanol to give 1-methoxycarbonyl-3-(2-aminophenyl)thiourea hydrochloride (5.1 g), m.p. 176°–178° C. (with decomposition).

By proceeding in a similar manner but substituting an equimolecular quantity of nitric acid and toluene-p-sulphonic acid for the hydrochloric acid, there were obtained 1-methoxycarbonyl-3-(2-aminophenyl)thiourea nitrate, m.p. 158°–159° C. (with decomposition), and 1-methoxycarbonyl-3-(2-aminophenyl)thiourea toluene-p-sulphonate, m.p. 175°–176° C. (with decomposition), respectively.

It is known, for example from British Patent No. 1214415 granted to Nippon Soda Company Limited on an Application filed 13th June 1969, that compounds of the general formula:

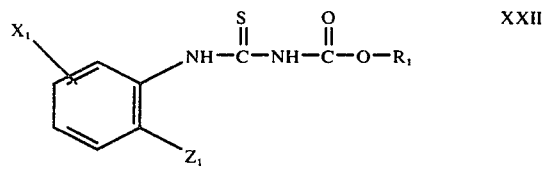

XXII wherein $X_1$ represents a hydrogen or chlorine atom or a nitro or methyl group, $R_1$ represents an alkyl group containing from 1 to 4 carbon atoms, and $Z_1$ represents a group —$NR_2R_3$, —$NR_2R_3A_1$ or —$N=R_4$ (wherein $R_2$ represents a hydrogen atom or a methyl group, $R_3$ represents a hydrogen atom, a methyl or formyl group, an alkanoyl group containing 2 or 3 carbon atoms, a cyclopropylcarbonyl or benzoyl group, an alkoxycarbonly group containing 2 or 3 carbon atoms, an alkylamino-carbonyl group containing 4 or 5 carbon atoms, a thioformyl or aminothiocarbonyl group, an aminothiocarbonyl group substituted by an alkyl group containing from 1 to 3 carbon atoms, or a 3,3-dimethylureidocarbonyl or 3,3-dimethylthioureidocarbonyl group, $R_4$ represents a benzal group or a benzal group substituted by a chlorine atom or a nitro or methoxy group and $A_1$ represents an organic or inorganic acid), possess fungicidal and acaricidal properties. There is no mention in the patent that the compounds have useful anthelmintic or anti-viral properties.

The invention also includes within its scope, as new and useful compounds, those benzene derivatives of general formula I wherein R, R¹ and R² and Y are as hereinbefore defined with the provisos that when R is an alkyl group containing not more than 4 carbon atoms, and (a) Y is a group —NR³R⁴ in which R³ is a hydrogen atom or a methyl group and R⁴ is an alkanoyl group containing 1 to 3 carbon atoms, a cyclopropylcarbonyl group or an alkoxycarbonyl group containing 2 or 3 carbon atoms, R² is other than a hydrogen or chlorine atom or a methyl group, or (b) Y is a group —NR³R⁴ in which R³ and R⁴ each represents a hydrogen atom, R² is other than a hydrogen or halogen atom or methyl group. For convenience in referring hereinafter to these new compounds of the invention they will be identified as a class by reference to "general formula XXII" although no formula will actually be depicted.

Examples of groups of compounds within this class of new benzene derivatives are:

a. Compounds wherein R is a straight- or branched-chain alkynyl group containing not more than 4 carbon atoms, e.g. propargyl, or a straight- or branched-chain aliphatic hydrocarbon group containing not more than 4 carbon atoms substituted by a halogen atom or an alkoxy group containing not more than 4 carbon atoms, e.g. 2-chloroethyl or 2-ethoxyethyl, R² is a hydrogen atom and Y is primary amino.

b. Compounds wherein R is a straight- or branched-chain aliphatic hydrocarbon group containing not more than 4 carbon atoms, e.g. methyl, ethyl or allyl, R² is a straight- or branched-chain alkyl group containing 2 to 4 carbon atoms, e.g. n-butyl, a straight- or branched-chain alkanoyl group containing 2 to 4 carbon atoms, e.g. acetyl, or a straight- or branched-chain alkoxycarbonylamino group containing 2 to 4 carbon atoms, e.g. methoxy-carbonylamino or isopropoxycarbonylamino and Y is a group —NHR⁴, wherein R⁴ is a hydrogen atom or a straight- or branched-chain alkanoyl group containing 1 to 4 carbon atoms optionally substituted by a cycloalkyl group containing 3 to 6 carbon atoms, e.g. formyl, acetyl or cyclopropylcarbonyl, or a straight- or branched-chain alkoxycarbonyl group containing 2 to 4 carbon atoms, e.g. methoxycarbonyl or ethoxycarbonyl.

c. Compounds wherein R is a straight- or branched-chain aliphatic hydrocarbon group containing not more than 4 carbon atoms, e.g. methyl or ethyl, R² is a hydrogen atom, a straight- or branched-chain alkyl group containing not more than 4 carbon atoms, e.g. n-butyl, or a straight- or branched-chain alkoxycarbonylamino group containing 2 to 4 carbon atoms, e.g. methoxycarbonylamino or isopropoxycarbonylamino and Y is a group -NHCOAZ [wherein Z is a carboxy group and A is a straight chain hydrocarbon group containing 2 to 4 carbon atoms, e.g. ethylene, vinylene, or Z represents a group of the general formula:

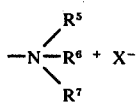

(wherein R⁵ is a hydrogen atom or a methyl group, R⁶ is a straight- or branched-chain alkyl group containing not more than 4 carbon atoms, e.g. methyl, ethyl or n-butyl, or a benzyl group, R⁷ represents a straight- or branched-chain alkyl group containing not more than 4 carbon atoms, e.g. methyl, ethyl, or n-butyl, or R⁶ and R⁷ together with the nitrogen atom to which they are attached form a piperidino, morpholino, 2,6-dimethyl-morpholino or 4-methylpiperazin-1-yl group, and X⁻ represents a halide ion, e.g. a chloride or iodide ion, or a methanesulphonate ion) or Z represents a group -NR⁶R⁷ (wherein R⁶ represents a straight- or branched-chain alkyl group containing not more than 4 carbon atoms, e.g. methyl, ethyl or n-butyl, or a benzyl group, R⁷ represents a straight- or branched-chain alkyl group containing not more than 4 carbon atoms, e.g. methyl, ethyl or n-butyl, or R⁶ and R⁷ together with the nitrogen atom to which they are attached form a piperidino, morpholino, or 4-methylpiperazin-1-yl group) and A represents a methylene or ethylene group, or a methylene group substituted by a methyl group[.

Also included within this invention, as a new compound is 1-ethoxycarbonyl-3-(2-amino-4-fluorophenyl)-thiourea.

In addition to possessing anthelmintic and antiviral acitivity, the new compounds of general formula XXII are also useful as agricultural pesticides, in particular as fungicides against species of fungi which are pathogenic to plants, and are also active as fungicides against fungal species which are pathogenic to animals, in particular *Trichophyton mentagrophytes*.

As fungicides for use against species of fungi pathogenic to plants, the new compounds of general formula XXII are particulary useful in the control of *Alternaria solani, Botrytis cinerea, Ceropora beticola, Cladosporium fulvum, Collectotrichum lagenarium, Corynespora melongenae, Elsinoe fawcetti, Erysiphe graminis, Fusarium sambucinum, Glomerella cingulata, Helminthosporium spp.*, e.g. *H. signoideum* and *H. avenae, Mycosphaerella spp.*, e.g. *M. pomi* and *M. pinodes, Pellicularia sasaki, Penicillium spp., Phaeoisariopsis vitis, Piricularia oryzae, Podosphaerea leucotricha, Pseudoperonospora humuli, Sclerotinia spp.*, e.g. *S. cinerea* and *S. slerotiorum, Sphaerotheca, spp.*, e.g. *S. fuliginea* and *S. humuli* and *Venturia inaequalis*.

Compounds of the invention which have useful fungicidal properties are, for example, 1-methoxycarbonyl-3-(2-dimethylaminoacetamidophenyl)thiourea hydrochloride, 1-methoxycarbonyl-3-(2-trimethylammoniumacetamidophenyl)-thiourea iodide, 1-ethoxycarbonyl-3-(2-dimethylaminoaet-amidophenyl)thiourea hydrochloride, 1-methoxycarbonyl-3-(2-amino-4-n-butylphenyl)thiourea, 1-metoxycarbonyl-3-(2-acetamido-4-n-butylphenyl)thiourea, 1-methoxycarbonyl-3-(4-n-butyl-2-ethoxycarbonylaminophenyl)thiourea, 1-ethoxy-carbonyl-3-(2-amino-4-fluorophenyl)-thiourea, 1-ethoxycarbonyl-3-(2-benzyl-N-methylaminoacetamidophenyl)thiourea hydrochloride, 1-ethoxycarbonyl-3-(2-trimethylammoniumacetamidophenyl)-thiourea iodide, 1-etoxycarbonyl-3-(2-di-n-butylaminoacetamidophenyl)thiourea hydrochloride, 1-ethoxycarbonyl-3-[2-(N-methyl-N-n-butylaminoacetamido)phenyl]thiourea hydrochloride, 1-ethoxycarbonyl-3-(2-piperidinoacetamid-phenyl)thiourea hydrochloride, 1-methoxycarbonyl-3-(2-dimethylaminopropionamidophenyl)thiourea hydrochloride, 1-ethoxycarbonyl-3-(2-diethylaminoacetamidophenyl)thiourea hydrochloride, and 1-ethoxycarbonyl-3-(2-morpholinoacetamidophenyl)thiourea hydrochloride.

The compounds falling within the scope of general formula I wherein R, R¹ and R² are as hereinbefore defined and Y represents a group —NR³R⁴ wherein R³ represents a hydrogen atom or a methyl group and R⁴ represents a group —COAZ (wherein A is as hereinbefore defined and Z represents a group of general formula II wherein R⁵, R⁶ R⁷ are as hereinbefore defined and X⁻ represents a pharmaceutically acceptable or agriculturally acceptable anion) are particularly valuable as anthelmintics and fungicides because of their high water-solubility. The term 'agriculturally acceptable anion' means an anion which is generally regarded as acceptable for use in agricultural practice, being relatively innocuous to the vegetable organism when used in fungicidal rates of application, so that the beneficial properties of the cation are not vitiated by side-effects ascribable to that anion. Halide ions and the methanesulphonate ion are good examples of such ions.

The new compounds of general XXII may be used as fungicides against fungi pathogenic to plants in the form of fungicidal composition, suitable for use in agriculture, containing as active ingredient at least one of the benzene derivatives of general formula XXII in association with one or more diluents compatible with the benzene derivatives and suitable for use in fungicidal compositions. Preferably the compositions contain between 0.005% and 95% by weight of the compounds of general formula XXII. Suitable solid diluents include aluminium silicate, kieselguhr, tricalcium phosphate, powdered cork, adsorbent carbon black, magnesium silicate, a clay such as kaolin, bentonite or attapulgite or a compatible solid wetting, dispersing or emulsifying agent. The compositions containing solid diluents, which may take the form of dusts or wettable powders, are prepared by impregnating the solid diluents with solutions of the compounds of general formula XXII in volatile solvents and evaporating the solvents, or by injecting those compounds of general formula XXII which are viscous liquids at room temperature, under high pressure into a suitable powder-blender containing the solid diluent or diluents, and, it necessary, grinding the product so as to obtain powders.

The wetting, dispersing and emulsifying agents which may be present, particularly in wettable powders, may be of the ionic or non-ionic types, for example, sulphoricinoleates, quaternary ammonium derivatives or products based upon condensates of ethylene oxide with nonyl and octyl phenol, or fatty acid esters of anhydrosorbitols which have been rendered soluble by etherification of the free hydroxy groups by condensation with ethylene oxide, or mixtures of these types of agents. Wettable powders according to the present invention may be treated with water immediately before use to give suspensions ready for application.

Liquid compositions may take the form of solutions, suspensions and emulsions of the compounds of general formula XXII which may, if desired, incorporate wetting, dispersing or emulsifying agents. These emulsions, suspensions and solutions may be prepared using aqueous, organic or aqueous-organic diluents, for example acetophenone, isophorone, toluene, xylene and mineral, animal or vegetable oils (and mixtures of these diluents), which may contain wetting, dispersing or emulsifying agents of the ionic or non-ionic types or mixtures thereof, for example those of the types described above. When desired, the emulsions containing the compounds of general formula XXII may be used in the form of self-emulsifying concentrates containing the active substances dissolved in the emulsifying agents or in solvents containing emulsifying agents compatible with the active substance, the simple addition of water to such concentrates producing compositions ready for use. Fungicidal compositions in the form of aerosols containing the compounds of general formula XXII are also within the scope of the present invention. If desired, the fungicidal compositions according to the present invention may contain other adjuvants such as adhesives.

Accordingly, there is provided a method for the destruction of fungi pathogenic to plants which comprises the application of the fungicidal compositions comprising compounds of general formula XXII, if necessary after suitable dilution, to crop-growing areas infested with these fungi. By the term 'crop-growing areas' is meant areas in which economically valuable crops are growing. Preferably the fungicidal compositions are applied at rates of from 0.5 to 3 lbs. of benzene derivative per acre, more particularly in the form of aqueous sprays prepared by diluting concentrates with water.

The new compounds of general formula XXII may be used as fungicides against fungi pathogenic to animals in the form of therapeutically useful compositions comprising at least one of the compounds in association with a pharmaceutically-acceptable carrier or coating of the type hereinbefore described as suitable for the use of compounds of general formula I as anthelmintics and antiviral agents. Therapeutically useful compositions comprising at least one of the new compounds of general formula XXII for use against fungi pathogenic to animals may be formulations suitable for topical application, e.g. lotions, ointments or creams.

The following Examples illustrate the preparation of new compounds according to the present invention:

EXAMPLE 1

2-Chloroethyl chloroformate (14.3 g; 0.10 mole) was added dropwise to a stirred suspension of potassium thiocyanate (11.7 g; 0.12 mole) in dry acetonitrile (100 ml). The temperature of the reaction mixture rose spontaneously to 40° C. and stirring was continued for two hours at 30° C. to 40° C. The reaction mixture was then filtered and the clear filtrate was added dropwise during fifteen minutes to a stirred suspension of o-phenylenediamine (10.8 g; 0.10 mole) in dry acetonitrile (50 ml), the temperature during the addition being maintained between 15°C. and 20° C. by external cooling. When the addition was complete the reaction mixture was stirred at 30° to 40° C. for two hours, and poured into water (1litre). The crude solid which separated was filtered off, washed with water and crystallised from methanol to give 1-(2-chloroethoxycarbonyl)-3-(2-aminophenyl)thiourea (14.9 g), m.p. 173°–174°C. (with decomposition).

By proceeding in a similar manner but substituting the appropriate quantities of propargyl chloroformate and 2-ethoxyethyl chloroformate for the 2-chloroethyl chloroformate, there were obtained 1-propargyloxycarbonyl-3-(2-aminophenyl)thiourea, m.p. 153°–155° C. (with decomposition) and 1-(2-ethoxyethoxycarbonyl)-3-(2-aminophenyl)thiourea, m.p. 128°–130° C.

EXAMPLE 2

Methyl chloroformate (18.4 g; 0.195 mole) was added dropwise to a stirred suspension of potassium thiocyanate (20.8 g; 0.214 mole) in dry acetonitrile (150 ml), the temperature of the reaction mixture being kept between 20° and 22° C. by slight external cooling, and stirring was continued at 30°–35° C. for two hours. The reaction mixture was then cooled in an ice bath to 15° C and 2-cyclopropylcarbonamido-5-n-butylaniline (22.6 g; 0.0974 mole) was added in portions during ten minutes, the temperature of the reaction mixture being maintained between 15° C. and 20° C. during the addition. When the addition was complete, the reaction mixture was stirred at laboratory temperature for 2 hours and poured into water (1litre). The crude solid which separated was filtered off, washed with water, dried and crystallised from ethyl acetate to give 1-methoxycarbonyl-3-(2-cyclopropylcarbonamido-5-n-butylphenyl)thiourea (25.7 g), m.p. 178°–180° C. (with decomposition).

By proceeding in a similar manner but substituting an equimolar quantity of 2-acetamido-5-n-butylaniline, 5n-butyl-2-formamidoaniline, 5n-butyl-2-ethoxycarbonylaminoaniline, 2-formamido-5-isopropoxycarbonylaminoaniline and 2-acetamido-5-isopropoxycarbonylaminoaniline for the 2-cyclopropylcarbonamido-5-n-butylaniline, there were obtained 1-methoxycarbonyl-3-(2-acetamido-5-n-butylphenyl)thiourea, m.p. 178°–180° C. (with decomposition), 1-methoxycarbonyl-3-(5n-butyl-2-formamidophenyl)thiourea, m.p. 167°–169° C. (with decomposition), 1-methoxycarbonyl-3-(5-n-butyl-2-ethoxycarbonylaminophenyl)thiourea, m.p. 137°–139° C, 1-methoxycarbonyl-3-(2formamido-5-isopropoxycarbonylaminophenyl)thiourea, m.p. 198°–200° C. (with decomposition) and 1-methoxycarbonyl-3-(2-acetamido-5-isopropoxycarbonylaminophenyl)thiourea, m.p. 211°–213° C. (with decomposition), respectively.

By again proceeding in a similar manner but using an equimolecular amount of ethyl chloroformate for the methyl chloroformate and an equimolecular quantity of 5-isopropoxycarbonylamino-2-methoxycarbonylaminoaniline for the 2-cyclopropylcarbonamido-5-n-butylaniline, there was obtained 1-ethoxycarbonyl-3-(5-isopropoxycarbonylamino-2-methoxycarbonylaminophenyl)thiourea, m.p. 194°–195° C. (with decomposition).

2-Cyclopropylcarbonamido-5-n-butylaniline used as a starting material in the above preparation, was prepared as follows:-

2-Cyclopropylcarbonamido-5-n-butyl-1-nitrobenzene (29.8 g; 0.114 mole), platinum oxide (1.3 g) and ethanol (400 ml) were mixed together and shaken in an atmosphere of hydrogen at atmospheric pressure and laboratory temperature until uptake ceased (7.8 litres of hydrogen were absorbed). The mixture was filtered and the ethanol was removed from the filtrate by evaporation under reduced pressure to give a solid residue. This crude product was crystallised from benzene to give 2-cyclopropylcarbonamido-5-n-butylaniline (22.6 g), m.p. 139°–142° C.

In a similar manner but substituting an equimolecular quantity of 5-n-butyl-2-formamido-1-nitrobenzene, 2-acetamido-5-n-butyl-1-nitrobenzene, 5-n-butyl-2-ethoxycarbonylamino-1-nitrobenzene, 2-formamido-5-isopropoxycarbonylamino-1-nitrobenzene, 2-acetamido-5-isopropoxycarbonylamino-1-nitrobenzene and 5-isopropoxycarbonylamino-2-methoxycarbonylamino-1-nitrobenzene for the 2-cyclopropylcarbonamido-5-n-butyl-1-nitrobenzene, there were prepared 5-n-butyl-2-formamidoaniline, m.p. 114°–116° C., 2-acetamido-5-n-butylaniline, 5n-butyl-2-ethoxycarbonylaminoaniline, 2-formamido-5-isopropoxycarbonylaminoaniline, m.p. 175°–177° C., 2-acetamido-5-isopropoxycarbonylaminoaniline, m.p. 192°–193° C. and 5-isopropoxycarbonylamino-2-methoxycarbonylaminoaniline respectively.

(Where no physical constants are given for the above compounds, they were found difficult to purify as they rapidly darkened on exposure to the atmosphere, but were satisfactory as starting materials for the preparation of the appropriate thiourea derivative).

2-Cyclopropylcarbonamido-5-n-butyl-1-nitrobenzene used as a starting material in the above preparation, was prepared as follows:

4-n-Butyl-2-nitroaniline (20.0g; 0.103 mole) was suspended in dry toluene (200 ml) and cyclopropane carbonyl chloride (12.0 g; 0.133 mole) was added dropwise to the stirred suspension. The mixture was then refluxed with stirring for ninety minutes. On cooling the clear solution deposited a yellow solid which was crystallised from light petroleum (b.p. 60°–80° C.) to give 2-cyclopropylcarbonamido-5-n-butyl-1-nitrobenzene (25.5 g), m.p. 83°–84° C.

By again proceeding in a similar manner but substituting an equimolecular quantity of acetyl chloride and ethyl chloroformate for cyclopropane carbonyl chloride, there were obtained 2-acetamido-5-n-butyl-1-nitrobenzene, m.p. 72°–73° C. and 5n-butyl-2-ethoxycarbonylamino-1-nitrobenzene, b.p. 136° C./0.2 mm.Hg. respectively.

By again proceeding in a similar manner but substituting an equimolecular quantity of acetyl chloride and methyl chloroformate for the cyclopropane carbonyl chloride and by substituting an equimolecular quantity of 4-isopropoxycarbonylamino-2-nitroaniline for the 4-n-butyl-2-nitroaniline, there were prepared 2-acetamido-5-isopropoxycarbonylamino-1-nitrobenzene, m.p. 163°–166° C., and 5-isopropoxycarbonylamino-2-methoxycarbonylamino-1-nitrobenzene, m.p. 168°–170° C. respectively.

5-n-Butyl-2-formamido-1-nitrobenzene, used as a starting material in the above preparation, was prepared as follows:

4-n-Butyl-2-nitroaniline (25-g; 0.13 mole) and formic acid (25 g; 0.54 mole) were mixed together at laboratory temperature and the mixture was then refluxed for forty minutes. After cooling to laboratory temperature the clear solution was poured into water (500 ml) and the orange solid which separated was filtered off, washed with water, dried and crystallised from light petroleum (b.p. 60°–80° C.) to give 5-n-butyl-2-formamido-1-nitrobenzene (20 g), m.p. 72°–73° C.

In a similar manner to that described above for the preparation of 5-n-butyl-2-formamido-1-nitrobenzene but substituting an equimolecular quantity of 4-isopropoxycarbonylamino-2-nitroaniline for the 4-n-butyl-2-nitroaniline, there was obtained 2-formamido-5-isopropoxycarbonylamino-1-nitrobenzene, m.p. 168°–170° C.

EXAMPLE 3

1-Methoxycarbonyl-3-(4n-butyl-2-nitrophenyl)-thiourea (69.0 g; 0.22 mole) and ferrous chloride tetrahydrate (9.2 g) were finely powdered together and suspended in a mixture of methanol (350 ml) and water (70 ml). The vigorously stirred suspension was then heated to reflux and reduced iron powder (42.0 g; 0.78 mole) was added in portions during forty-five minutes. When the addition was complete, the reaction mixture was refluxed for a further thirty minutes and filtered. On cooling a crystalline solid separated from the filtrate. The dark brown filter cake was extracted with boiling methanol (3 × 200 ml) and the combined methanol extracts were evaporated to dryness to give a solid residue. This was combined with the solid obtained from the cold filtrate and the combined solids were crystallised from methanol to give 1-methoxycarbonyl-3-(2-amino-4-n-butylphenyl)thiourea (51.0 g), m.p. 157°–159° C. (with decomposition).

By proceeding in a similar manner but substituting equimolecular quantities of 1-methoxycarbonyl-3-(4- isopropoxycarbonylamino-2-nitrophenyl)thiourea, 1-methoxycarbonyl-3-(4-methoxycarbonylamino-2-nitrophenyl)thiourea, 1-ethoxycarbonyl-3-(4n-butyl-2-nitrophenyl)thiourea, 1-ethoxycarbonyl-3-(4-isopropoxycarbonylamino-2-nitrophenyl)thiourea and 1-methoxycarbonyl-3-(4-acetyl-2-nitrophenyl)thiourea, there were obtained 1-methoxycarbonyl-3-(2amino-4-isopropoxycarbonylaminophenyl)thiourea, m.p. 198°–200° C. (with decomposition), 1-methoxycarbonyl-3-(2-amino-4-methoxycarbonylaminophenyl)thiourea, m.p. 190°–102° C. (with decomposition), 1-ethoxycarbonyl-3-(2-amino-4-n-butylphenyl)thiourea, m.p. 152°–154° C., 1-ethoxycarbonyl-3-(2-amino-4-isopropoxycarbonylaminophenyl)thiourea, m.p. 204°–206° C. (with decomposition) and 1-methoxycarbonyl-3-(4-acetyl-2-aminophenyl)thiourea, m.p. 193°–194° C. (with decomposition), respectively.

EXAMPLE 4

Acetyl chloride (4.53 g.; 0.058 mole) was added to a suspension of 1-methoxycarbonyl-3-(2-amino-4-n-butylphenyl)-thiourea (16.0 g; 0.057 mol3) in dry toluene (230 ml) and the stirred mixture was refluxed for ninety minutes. During this time the solid gradually dissolved to give a slightly turbid solution. On cooling to laboratory temperature a solid separated which was filtered off and recrystallised to give 1-methoxycarbonyl-3-(2-acetamido-4-n-butylphenyl)thiourea (11.4 g), m.p. 173°–174° C. (with decomposition).

By proceeding in a similar manner but substituting an equimolecular quantity of cyclopropanecarbonyl chloride and ethyl chloroformate for the acetyl chloride, there were obtained 1-methoxycarbonyl-3-(4-n-butyl-2-cycloproplycarbonamidophenyl)thiourea, m.p. 187°–180° C. (with decomposition) and 1-methoxycarbonyl-3-(4-n-butyl-2-ethoxycarbonylaminophenyl)thiourea, m.p. 141°–143° C. (with decomposition), respectively.

By proceeding in a similar manner but substituting an equimolecular quantity of 1-methoxycarbonyl-3-(2-amino-4-isopropoxycarbonylaminophenyl)thiourea and 1-ethoxycarbonyl-3-(2-amino-4-isopropoxycarbonylaminophenyl)thiourea for 1-methoxycarbonyl-3-(2-amino-4-n-butylphenyl)thiourea, there were obtained 1-methoxycarbonyl-3-(2-acetamido-4-isopropoxycarbonylaminophenyl)thiourea, m.p. 187°–188° C. (with decomposition) and 1-ethoxycarbonyl-3-(2-acetamido-4-isopropoxycarbonylaminophenyl)thiourea, m.p. 201°–202° C. (with decomposition), respectively.

EXAMPLE 5

1-Methoxycarbonyl-3-(2-amino-4-n-butylphenyl)thiourea (15.0 g; 0.053 mole) and formic acid (18.4 g; 0.4 mole) were mixed together at laboratory temperature and the mixture was refluxed for forty minutes. The hot clear solution was then poured into water, and the solid which separated was filtered off, washed with water, dried and crystallised from 2-ethoxyethanol to give 1-methoxycarbonyl-3-(4-n-butyl-2-formamidophenyl)thiourea (12.0 g), m.p. 182°–183° C. (with decomposition).

By proceeding in a similar manner but substituting an equimolecular quantity of 1-methoxycarbonyl-3-(2-amino-4-isopropoxycarbonylaminophenyl)thiourea for the 1-methoxycarbonyl-3-(2-amino-4-n-butylphenyl)thiourea, there was obtained 1-methoxycarbonyl-3-(2-formamido-4-isopropoxycarbonylaminophenyl)thiourea, m.p. 194°–195° C. (with decomposition).

EXAMPLE 6

A suspension of N-(2-aminophenyl)-2-dimethylaminoacetamide (4.8 g) in dry acetonitrile (20 ml) was stirred vigorously during the dropwise addition of methoxycarbonyl isothiocyanate (3.5 g), the temperature being maintained between 15° C. and 20° C. by external cooling, and afterwards for a further 5 minutes. The mixture was then diluted with diethyl ether (500 ml) and treated with an excess of a saturated solution of hydrogen chloride in diethyl ether. The precipitate was filtered off, dissolved in the minimum quantity of water, and treated with an excess of a 2N aqueous solution of sodium hydroxide. The precipitate was filtered off and recrystallised twice from benzene to give 1-methoxycarbonyl-3-(2-dimethylaminoacetamidophenyl)thiourea (3.5 g), m.p. 130°–131° C. (with decomposition).

1-Methoxycarbonyl-3-(2-dimethylaminoacetamidophenyl)thiourea (3.0 g) was dissolved in the minimum quantity of ethanol and the solution treated with diethyl ether (300 ml), followed by an excess of a saturated solution of hydrogen chloride in diethyl ether. The resultant solid was filtered off and recrystallised from ethanol to give 1-methoxycarbonyl-3-(2-dimethylaminoacetamidophenyl)thiourea hydrochloride (2.8 g) m.p. 187°–188° C. (with decomposition).

Similarly, by substituting an excess of methanesulphonic acid for the solution of hydrogen chloride in diethyl ether, there was prepared 1-methoxycarbonyl-3-(2-dimethylaminoacetamidophenyl)thiourea methanesulphonate, m.p. 164°–165° C. (with decomposition).

The N-(2-aminophenyl)-2-dimethylaminoacetamide, used as a starting material in the above reaction, was prepared as follows:

A solution of dimethylamine in ethanol (40 ml. of a 33% w/w solution) was added to a suspension of N-(2-nitrophenyl)-2-chloroacetamide (14.9 g) [prepared by the method described by G. Tennant, J.C.S., (1963), 2428] in ethanol (70 ml) and the mixture was heated to reflux, with stirring, for 2hours. After cooling, the ethanol and excess dimethylamine were evaporated off under reduced pressure and the solid residue was treated with an aqueous potassium hydroxide solution (100 ml., 40% w/v). The resulting suspension was extracted with diethyl ether (3 × 100 ml) and the combined extracts dried over magnesium sulphate and evaporated to give N-(2-nitrophenyl)-2-dimethylaminoacetamide (13.8 g), m.p. 44°–47° C., sufficiently pure to be used in the next stage of the synthesis, the preparation of N-(2-aminophenyl)-2-dimethylaminoacetamide.

N-(2-nitrophenyl)-2-dimethylaminoacetamide (13.8 g), platinum oxide (0.2 g) and ethanol (100 ml) were mixed together and shaken in an atmosphere of hydrogen at atmospheric pressure and laboratory temperature until absorption of hydrogen ceased (4.5 litres of hydrogen were absorbed in 2hours). The mixture was then filtered and the ethanol evaporated off under reduced pressure. The solid residue so obtained was recrystallised from cyclohexane to give N-(2-aminophenyl)-2-dimethylaminoacetamide (9.3 g), m.p. 121°–123° C.

N-(2-Aminophenyl)-2-dimethylaminoacetamide may also be prepared as follows:

A solution of N-(2-nitrophenyl)-2-chloroacetamide (4.29 g) in ethanol (80 ml) containing platinum oxide catalyst (0.15 g) was shaken in an atmosphere of hydrogen, at atmospheric pressure and laboratory temperature, until 1.5 litres of hydrogen had been absorbed. The mixture was filtered. The filtrate was evaporated under reduced pressure and the residual solid triturated with water. The solid obtained, m.p. 79°–85° C., was filtered off and dissolved in ethanol. A solution of dimethylamine in ethanol (20% w/w; 10 ml) was added and the mixture heated under reflux for 2 hours. The ethanol was then evaporated under reduced pressure and water (20 ml) added to the residue. The mixture obtained was extracted with diethyl ether (3 × 50 ml) and the ethereal extracts dried over magnesium sulphate and evaporated to dryness. The residual solid was recrystallised twice from cyclohexane to give N-(2-aminophenyl)-2-dimethylaminoacetamide, m.p. 119°–121° C.

The methoxycarbonyl isothiocyanate, used as a starting material in the above preparation of 1-methoxycarbonyl-3-(2-dimethylaminoacetamidophenyl)thiourea, was prepared as follows:

Methyl chloroformate (94.5 g) was slowly added to a stirred suspension of dry potassium thiocyanate (106.7 g) in dry acetone (400 ml) at 40° C., maintained at that temperature by external cooling. The mixture was stirred for a further hour, the temperature being allowed to return to that of the laboratory.

It was then filtered and the filtrate evaporated to dryness under reduced pressure. The residue so obtained was treated with diethyl ether (500 ml). The mixture was filtered and diethyl ether removed from the filtrate by evaporation under reduced pressure to give an oil, which was distilled to give methoxycarbonyl isothiocyanate (30.0 g), b.p. 32°–33° C./15 mm.Hg.

EXAMPLE 7

A suspension of 1-methoxycarbonyl-3-(2-chloroacetamidophenyl)thiourea (1.51 g) in benzene (50 ml) was treated with a solution of dimethylamine in benzene (15 ml., 10% w/w). The mixture was heated to reflux for 15 minutes with stirring. A further quantity of dimethylamine in benzene (5ml, 10% w/w) was added, and the mixture heated to reflux for a further 15 minutes with stirring. The mixture was allowed to stand for 1 hour, during which time it cooled to room temperature, and was then filtered. The filtrate was treated with an excess of a saturated solution of hydrogen chloride in diethyl ether. The precipitate was filtered off, treated with water (20 ml), some insoluble solid was filtered off, and the aqueous filtrate neutralised by treatment with 2N aqueous sodium hydroxide solution. The resultant solid was filtered off, dissolved in the minimum quantity of ethanol and the solution treated with diethyl ether, followed by an excess of a saturated solution of hydrogen chloride in diethyl ether. The resultant solid was filtered off and recrystallised from ethanol to give 1-methoxycarbonyl-3-(2-dimethylaminoacetamidophenyl)thiourea hydrochloride (0.25 g), m.p. 187°–188° C. (with decomposition).

The 1-methoxycarbonyl-3-(2-chloroacetamidophenyl)-thiourea, used as a starting material in the above preparation, was prepared as follows:

A suspension of 1-methoxycarbonyl-3-(2-aminophenyl)thiourea (9.00 g) in toluene (80 ml) was treated with chloroacetyl chloride (4.52 g) at room temperature and the mixture was heated to reflux for 1 hour with stirring. The mixture was then cooled to room temperature and the resultant white solid was filtered off and recrystallised from ethanol to give 1-methoxycarbonyl-3-(2-chloroacetamidophenyl)thiourea (7.98 g ), m.p. 156°–158° C.

The 1-methoxycarbonyl-3-(2-aminophenyl)thiourea, used as a starting material in the above preparation, was prepared as follows:

Potassium thiocyanate (24.2 g), methyl chloroformate (23.6 g) and dry acetone (150 ml) were mixed with stirring at laboratory temperature. The temperature of the reaction mixture rose spontaneously to 51° C. and stirring was continued for two hours at 45° C. to 51° C. The reaction mixture was then cooled in an ice-bath to a temperature of 15° C. and o-phenylenediamine (27.0 g) was then added in portions, with stirring, over a period of fifteen minutes, the temperature of the stirred reaction mixture being maintained between 15° C. and 20° C. during the addition. When the addition was complete, the reaction mixture was sitrred at laboratory temperature for eighteen hours and then filtered. The solid residue was washed with water and dried in a vacuum desiccator to give a crude product (5.0 g), m.p. 189° C. (with decomposition).

The crude product was recrystallised from dry ethanol (40 ml) to give 1-methoxycarbonyl-3-(2-aminophenyl)thiourea (3.5 g), m.p. 189°–190° C. (with decomposition).

EXAMPLE 8

A suspension of N-(2-aminophenyl)-2-dimethylaminoacetamide (8.9 g) (prepared as described in Example 6) in acetonitrile (50 ml) was treated with ethoxycarbonyl isothiocyanate (6.4 g), dropwise with stirring, maintaining the temperature at 15°–20° C. by external cooling. When the addition was complete, the solid had dissolved but after being left to stand for a further 5 minutes, another solid precipitated. This was filtered off and washed with ice-cold acetonitrile to give 1-ethoxycarbonyl-3-(2-dimethylaminoacetamidophenyl)thiourea (9.4 g), m.p. 159°–160° C. (with decomposition).

By proceeding in a similar manner but substituting N-(2-aminophenyl)-2-(N-benzyl-N-methylamino)-acetamide, N-(2-aminophenyl)-2-piperidinoacetamide and N-(2-aminophenyl)-2-(4-methylpiperazin-1-yl)acetamide for the N-(2-aminophenyl)-2-dimethylaminoacetamide, there were prepared 1-ethoxycarbonyl-3-[2-(N-benzyl-N-methylaminoacetamido)-phenyl]thiourea, m.p. 176°–178° C. (with decomposition), 1-ethoxycarbonyl-3-(2-piperidinoacetamidophenyl)thiourea, m.p. 154°–158° C. (with decomposition) and 1-ethoxycarbonyl-3-[2-(4-methylpiperazin-1-ylacetamido)phenyl]thiourea, m.p. 183°–185° C. (with decomposition), respectively.

1-Ethoxycarbonyl-3-(2-dimethylaminoacetamidophenyl)thiourea (5.0 g) was dissolved in the minimum quantity of ethanol and the solution treated with diethyl ether (500 ml), followed by a saturated solution of hydrogen chloride in diethyl ether. The resultant solid was filtered off and recrystallised from ethanol/-diethyl ether to give 1-ethoxycarbonyl-3-(2-dimethylaminoacetamidophenyl)thiourea hydrochloride (4.3 g), m.p. 178°–180° C. (with decomposition).

By proceeding in a similar manner but substituting 1-ethoxycarbonyl-3-[2-(N-benzyl-N-methylaminoacetamido)phenyl]-thiourea, 1-ethoxycarbonyl-3-(2-piperidinoacetamidophenyl)- thiourea and 1-ethoxycarbonyl-3-[2-(4-methylpiperazin-1-yl-acetamido)phenyl]thiourea for the 1-ethoxycarbonyl-3-(2-dimethylaminoacetamidophenyl)thiourea, there were prepared 1-ethoxycarbonyl-3-[2-(N-benzyl-N-methylaminoacetamido)-phenyl]thiourea hydrochloride, m.p. 187°–188° C. (with decomposition), 1-ethoxycarbonyl-3-(2-piperidinoacetamidophenyl)thiourea hydrochloride, m.p. 179°–180° C. (with decomposition) and 1-ethoxycarbonyl-3-[2-(4-methylpiperazin-1-ylacetamido)phenyl]thiourea hydrochloride, m.p. 193°–195° C. (with decomposition).

By proceeding in a similar manner to that described above for the preparation of 1-ethoxycarbonyl-3-(2-dimethylaminoacetamidophenyl)thiourea but substituting N-(2-amino-4-isopropoxycarbonylaminophenyl)acetamide and N-(2-aminophenyl)-2-morpholinoacetamide for the N-(2-aminophenyl)-2-dimethylaminoacetamide and treating the bases obtained with ethereal hydrogen chloride as described above for the preparation of 1-ethoxycarbonyl-3-(2-dimethylaminoacetamidophenyl)thiourea hydrochloride, there were prepared 1-ethoxycarbonyl-3-(2-dimethylaminoacetamido-5-isopropoxycarbonylaminophenyl)-thiourea hydrochloride, m.p. 159°–161° C. (with decomposition), and 1-ethoxycarbonyl-3-(2-morpholinoacetamidophenyl)thiourea hydrochloride, m.p. 187°–189° C. (with decomposition), respectively.

By proceeding in a similar manner to that described in Example 6 for the preparation of methoxycarbonyl isothiocyanate, but substituting an equimolar quantity of ethyl chloroformate for the methyl chloroformate, there was prepared ethoxycarbonyl isothiocyanate, b.p. 55°–57° C./15 mm. Hg, used as a starting material in the above preparation.

N-(2-Aminophenyl)-2-(N-benzyl-N-methylamino)-acetamide, used as a starting material in two of the above preparations, was obtained as follows:-

A mixture of N-(2-nitrophenyl)-2-chloroacetamide (21.4 g), N-benzylmethylamine (24.2 g) and ethanol (200 ml) was heated under reflux for 2 hours. The ethanol was then removed under reduced pressure and water (500 ml) added to the residue. The mixture obtained was extracted with diethyl ether and the ethereal extract dried over magnesium sulphate and evaporated to dryness to give N-(2-nitrophenyl)-2-(N-benzyl-N-methylamino)acetamide (29.9 g), m.p. 84°–85° C.

By proceeding in a similar manner but substituting corresponding amounts of piperidine, morpholine and N-methylpiperazine for the N-benzylmethylamine, there were prepared N-(2-nitrophenyl)-2-piperidinoacetamide, m.p. 79°–81° C., N-(2-nitrophenyl)-2-morpholinoacetamide, m.p. 133°–135° C. (with decomposition) and N-(2-nitrophenyl)-2-(4-methylpiperazin-1-yl)acetamide, m.p. 56°–58° C.

Furthermore, by replacing the N-benzylmethylamine by dimethylamine and the N-(2-nitrophenyl)-2-chloroacetamide by N-(4-isopropoxycarbonylamino-2-nitrophenyl)-2-bromoacetamide and proceeding in a similar manner to that described above, there was prepared N-(4-isopropoxycarbonylamino-2-nitrophenyl)-2-dimethylaminoacetamide, m.p. 159°–160° C.

The N-(4-isopropoxycarbonylamino-2-nitrophenyl)2-bromoacetamide, used as a starting material in the above reaction, was prepared as follows:

Bromoacetyl bromide (18.6 g) was added dropwise with stirring to a solution of 4-isopropoxycarbonylamino-2-nitroaniline (22g) in toluene (300 ml). The solution was refluxed for 1 hour, cooled, and the solid filtered off and recrystallised from benzene to give N-(4-isopropoxycarbonylamino-2-nitrophenyl)-2-bromoacetamide (20 g), m.p. 195°–197° C.

A suspension of N-(2-nitrophenyl)-2-(N-benzyl-N-methylamino)acetamide (30 g) and platinum oxide (0.3 g) in methanol (500 ml) was shaken in an atmosphere of hydrogen at laboratory temperature and atmospheric pressure until the uptake of hydrogen was complete. 6.6 Litres of hydrogen were absorbed. The mixture was filtered, and evaporated to dryness to give an oil which was extracted with boiling cyclohexane (1 litre). On cooling, N-(2-aminophenyl)-2-(N-benzyl-N-methylamino)acetamide (12.5 g) was obtained as off-white crystals, m.p. 75°–77° C.

Similarly, by replacing the N-(2-nitrophenyl)-2-(N-benzyl-N-methylamino)acetamide by N-(2-nitrophenyl)-2-piperidinoacetamide, N-(2-nitrophenyl)-2-morpholinoacetamide, N-(2-nitrophenyl)-2-(4-methylpiperazin-1-yl)acetamide and N-(4-isopropoxycarbonylamino-2-nitrophenyl)-2-dimethylaminoacetamide, there were prepared respectively N-(2-aminophenyl)-2-piperidinoacetamide, m.p.174°–176° C., N-(2-aminophenyl)-2-morpholinoacetamide, m.p. 198°–200° C. (with decomposition), N-(2-aminophenyl)-2-(4-methylpiperazin-1-yl)acetamide, m.p. 138°–140° C. (with decomposition), and N-(2-amino-4-isopropoxycarbonylaminophenyl)-2-dimethylaminoacetamide, m.p. 173°–175° C.

EXAMPLE 9

A solution of 1-ethoxycarbonyl-3-(2-dimethylaminoacetamidophenyl)thiourea (4.0 g) in ethyl acetate (50 ml) at about 35° C. was treated with methyl iodine (1 ml) with stirring. The mixture was allowed to cool and stand for 16 hours. The resultant solid was filtered off and recrystallised from ethanol to give 1-ethoxycarbonyl-3-(2-trimethylammoniumacetamidophenyl)thiourea iodide (3.5 g), m.p. 210°–211° C. (with decomposition).

By proceeding in a similar manner, but substituting 1-methoxycarbonyl-3-(2-dimethylaminoacetamidophenyl)thiourea for the 1-ethoxycarbonyl-3-(2-dimethylaminoacetamidophenyl)thiourea, there was prepared 1-methoxycarbonyl-3-(2-trimethylammoniumacetamidophenyl)thiourea iodide, m.p. 176°–178° C. (with decomposition).

EXAMPLE 10

Petroleum spirit (b.p. 60°–80° C; 50 ml) was added to a solution of N-(2-amino-4-n-butylphenyl)-2-dimethylaminoacetamide (4.98 g) in benzene (50 ml) and the solution stirred vigorously while ethoxycarbonyl isothiocyanate (2.65 g) was added dropwise, with external cooling, to maintain the temperature between 15° C. and 20° C. After ten minutes, the precipitated solid was filtered off and recrystallised from benzene to give crude 1-ethoxycarbonyl-3-(5-n-butyl-2-dimethylaminoacetamidophenyl)thiourea, m.p.152°–155° C. (with decomposition), which was then dissolved in the minimum of ethanol. Diethyl ether (200 ml) was added, followed by an excess of a saturated solution of hydrogen chloride in diethyl ether. The precipitated solid was filtered off and recrystallised from ethanol-/ethyl acetate to give 1-ethoxycarbonyl-3-(5-n-butyl-2-dimethylaminoacetamidophenyl)thiourea hydrochloride (1.9 g), m.p. 174°–176° C. (with decomposition).

By proceeding in a similar manner to that described above for the preparation of 1-ethoxycarbonyl-3-(5-n-butyl-2-dimethylaminoacetamidophenyl)thiourea but substituting N-(2-aminophenyl)-2-diethylaminoacetamide, N-(2-aminophenyl)-2-(N-methyl-N-n-butylamino)acetamide, N-(2-aminophenyl)-2-di-n-butylaminoacetamide and N-(2-aminophenyl)-2-dimethylaminopropionamide for the N-(2-amino-4-n-butylphenyl)-2-dimethylaminoacetamide, there were prepared 1-ethoxycarbonyl-3-(2-diethylaminoacetamidophenyl)thiourea, m.p. 159°–160° C. (with decomposition), 1-ethoxycarbonyl-3-(2-N-n-butyl-N-methylaminoacetamidophenyl)thiourea, m.p. 95°–98° C., 1-ethoxycarbonyl-3-(2-di-n-butylaminoacetamidophenyl)thiourea, m.p. 137°–139° C., and 1-ethoxycarbonyl-3[2-(1-dimethylaminoethylcarbonylamino)-phenyl]thiourea, m.p. 143°–144° C, respectively, which were then treated with ethereal hydrogen chloride as described above for the preparation of 1-ethoxycarbonyl-3-(5-n-butyl-2-dimethylaminoacetamidophenyl)-thiourea hydrochloride to give 1-ethoxycarbonyl-3-(2-diethylaminoacetamidophenyl)thiourea hydrochloride, m.p. 177°–179° C. (with decomposition), 1-ethoxycarbonyl-3-(2-N-n-butyl-N-methylaminoacetamidophenyl)thiourea hydrochloride, m.p. 181°–183° C. (with decomposition), 1-ethoxycarbonyl-3-(2-di-n-butylaminoacetamidophenyl)thiourea hydrochloride, m.p. 192°–194° C, (with decomposition), and 1-ethoxycarbonyl-3-[2-(1-dimethylaminoethylcarbonylamino)phenyl]thiourea hydrochloride, m.p. 194°–195° C. (with decomposition), respectively.

The N-(2-amino-4-n-butylphenyl)-2-dimethylaminoacetamide, used as a starting material in the above synthesis, was prepared as follows:

A suspension of N-(4-n-butyl-2-nitrophenyl)-2-bromoacetamide (41 g) in ethanol (200 ml) was treated with a solution of dimethylamine in ethanol (90 ml of 20% w/w). The mixture was refluxed for one hour and the ethanol was evaporated off. Water (100 ml) was added and the mixture extracted with diethyl ether (3 × 200 ml). The extract was dried over magnesium sulphate, filtered and evaporated to give N-(4-n-butyl-2-nitrophenyl)-2-dimethylaminoacetamide as a yellow oil which was used without further purification in the next stage.

Similarly, by replacing the N-(4-n-butyl-2-nitrophenyl)-2-bromoacetamide by N-(2-nitrophenyl)-2-bromopropionamide, there was prepared N-(2-nitrophenyl)-2-dimethylaminopropionamide as a red oil which was used without further purification in the next stage.

Similarly, by replacing the N-(4-n-butyl-2-nitrophenyl)-2-bromoacetamide by N-(2-nitrophenyl)-2-chloroacetamide and the dimethylamine with corresponding amounts of diethylamine, there was prepared N-(2-nitrophenyl)-2-diethylaminoacetamide, m.p. 68°–71° C.

N-(2-Nitrophenyl)-2-(N-n-butyl-N-methylamino)-acetamide may be prepared as follows:

N-(2-Nitrophenyl)-2-chloroacetamide (32.2 g) dissolved in benzene (350 ml) and N-n-butylmethylamine (26.1 g) added. The mixture was boiled under reflux for 22 hours, the benzene evaporated off, and water (300 ml) added. The mixture was extracted with diethyl ether (3 × 200 ml), the extract dried with magnesium sulphate, filtered, and the ether evaporated off to give N-(2-nitrophenyl)-2-(N-n-butyl-N-methylamino)acetamide as a yellow oil which was used in the next stage without purification.

Similarly, by replacing the N-n-butylmethylamine by di-n-butylamine in the above preparation, there was prepared N-(2-nitrophenyl)-2-(di-n-butylamino)acetamide as a yellow oil.

N-(4-n-butyl-2-nitrophenyl)-2-dimethylaminoacetamide (36 g), prepared as described above, platinum oxide (0.2 g) and ethanol (100 ml) were shaken together in an atmosphere of hydrogen at laboratory temperature and atmospheric pressure until the uptake of hydrogen was complete; 8.2 litres were absorbed. The mixture was filtered and the ethanol evaporated off. The resultant solid was recrystallised from petroleum spirit (b.p. 60°–80° C.) to give N-(2-amino-4-n-butylphenyl)-2-dimethylaminoacetamide (24.0 g), m.p. 63°–66° C.

Similarly by substituting N-(2-nitrophenyl)-2-diethylaminoacetamide, N-(2-nitrophenyl)-2-(N-n-butyl-N-methylamino)acetamide, N-(2-nitrophenyl)-2-di-n-butylaminoacetamide and N-(2-nitrophenyl)-2-dimethylaminopropionamide for the N-(2-nitro-4-n-butylphenyl)-2-dimethylaminoacetamide in the above preparation, there were prepared respectively N-(2-aminophenyl)-2-diethylaminoacetamide, m.p. 76°–77° C., N-(2-aminophenyl)-2-(N-n-butyl-N-methylamino)acetamide, m.p. 66°–68° C., N-(2-aminophenyl)-2-di-n-butylaminoacetamide, an oil whose dihydrochloride had an m.p. of 189°–191° C. with decomposition, and N-(2-aminophenyl)-2-dimethylaminopropionamide, an oil which was used without further purification in the next stage.

The N-(4-n-butyl-2-nitrophenyl)-2-bromoacetamide, which was used as a starting material for one of the above reactions, was prepared as follows:

A solution of 4-n-butyl-2-nitroaniline (29.1 g) in toluene (100 ml) was treated with bromoacetyl bromide (33.3 g). The mixture was boiled under reflux for 3/4 hour and the toluene evaporated off. The residual oil was poured into petroleum spirit (b.p. 60°–80° C; 400 ml). Crystals were deposited and these were removed by filtration to give N-(4-n-butyl-2-nitrophenyl)-2-bromoacetamide (41 g), m.p. 56°–57° C.

Similarly, by replacing the 4-n-butyl-2-nitroaniline by 2-nitroaniline, and the bromoacetyl bromide by 2-bromopropionyl chloride, there was prepared N-(2-nitrophenyl)-2-bromopropionamide, m.p. 57°–58° C.

EXAMPLE 11

Ethoxycarbonyl isothiocyanate (5.6 g) was added dropwise, with cooling to maintain the temperature between 15° and 20° C., to a vigorously stirred solution of N-(2-amino-4-methoxycarbonylaminophenyl)-2-dimethylaminoacetamide (10.75 g) in dry acetone (200 ml). The resulting mixture was stirred for a further 30 minutes and then poured into an excess of water. The precipitated solid was filtered off to give crude 1-ethoxycarbonyl-3-(2-dimethylaminoacetamido-5-methoxycarbonylaminophenyl)thiourea, m.p. 171°–172° C, which was then dissolved in the minimum of ethanol. Diethyl ether (300 ml) was added, followed by an excess of a saturated solution of hydrogen chloride in diethyl ether. The precipitated solid was filtered off and recrystallised from methanol/ethanol to give 1-ethoxycarbonyl-3-(2-dimethylaminoacetamido-5-methoxycarbonylaminophenyl)thiourea hydrochloride (7.5 g), m.p. 211°–213° C. (with decomposition).

The N-(2-amino-4-methoxycarbonylaminophenyl)-2-dimethylaminoacetamide, used as a starting material for the preceding reaction was prepared as follows:

4-Methoxycarbonylamino-2-nitroaniline (30 g) was dissolved in toluene (300 ml) and the solution treated with bromoacetyl bromide (28.7 g). The mixture was refluxed for 3 hours and toluene (300 ml) was added. The hot mixture was filtered and the filtrate allowed to cool to give N-(4-methoxycarbonylamino-2-nitrophenyl)-2-bromoacetamide (30 g), m.p. 160°–162° C.

N-(4-methoxycarbonylamino-2-nitrophenyl)-2-bromoacetamide (25 g) in ethanol (250 ml) was treated with a solution of dimethylamine in ethanol (35.5 g of a 30% w/w solution) and the mixture refluxed for one hour. The ethanol was evaporated and the residual solid shaken with water and filtered to give N-(4-methoxycarbonylamino-2-nitrophenyl)-2-dimethylaminoacetamide (21.1 g), m.p. 186°–189° C.

N-(4-methoxycarbonylamino-2-nitrophenyl)-2-dimethylaminoacetamide (25.3 g), platinum oxide (0.4 g) and methanol (250 ml) were shaken together in an atmosphere of hydrogen at atmospheric pressure and laboratory temperature until the uptake of hydrogen was complete. Six litres of hydrogen were absorbed. The mixture was filtered and the ethanol evaporated. The residual solid was recrystallised from isopropanol to give N-(2-amino-4-methoxycarbonylaminophenyl)-2-dimethylaminoacetamide (15.7 g), m.p. 140°–142° C.

The 4-methoxycarbonylamino-2-nitroaniline was prepared as follows:

Methyl chloroformate (34 g) was added dropwise with stirring to a mixture of 2-nitro-p-phenylenediamine (50 g), sodium bicarbonate (44.5 g) and water (700 ml). The temperature was maintained at 5° C. during the addition by means of external cooling. After the addition was complete the mixture was allowed to warm to room temperature and the stirring was continued for two hours. The solid was filtered off and recrystallised from isopropanol to give 4-methoxycarbonylamino-2-nitroaniline (50 g), m.p. 171°–172° C.

EXAMPLE 12

A suspension of dimethylamine in ethanol (20% w/w; 18 ml) was added to a suspension of 1-methoxycarbonyl-3-[2-(3-chloropropionamido)phenyl]thiourea (8.2 g) in ethanol (50 ml). The mixture was heated under reflux, with stirring, for 30 minutes, the ethanol removed by distillation and water (10 ml) added to the residual gum which slowly solidified. The solid was filtered off and dissolved in the minimum of ethanol. Diethyl ether (300 ml) was added, followed by an excess of a saturated solution of hydrogen chloride in diethyl ether. The precipitated solid was filtered off and recrystallised from ethanol to give 1-methoxycarbonyl-3-[2-(3-dimethylaminopropionamido)phenyl]thiourea hydrochloride (3.3 g), m.p. 182°–183° C. (with decomposition).

1-Methoxycarbonyl-3-[2-(3-chloropropionamido)-phenyl]thiourea used as starting material in the above preparation was prepared by heating a mixture of 1-methoxycarbonyl-3-(2-aminophenyl)thiourea (13.5 g), 3-chloropropionyl chloride (7.62 g) and toluene (100 ml) under reflux for 1½ hours. The mixture was then cooled and the precipitated solid filtered off, washed with cold toluene (20 ml) and recrystallised from ethanol to give 1-methoxycarbonyl-3[2-(3-chloropropionamido)phenyl]-thiourea (9.8 g) m.p. 191°–193° C. (with decomposition).

EXAMPLE 13

Exthoxycarbonyl isothiocyanate (5.1 g) was added dropwise, with stirring and cooling to maintain the temperature between 15°. and 20° C., to a solution of N-(2-aminophenyl)-trimethylammoniumacetamide chloride (9.1 g) in ethanol (250 ml). After stirring for a further 15 minutes, the precipitated solid was filtered off and recrystallised from ethanol to give 1-ethoxycarbonyl-3-(2-trimethylammoniumacetamidophenyl)thiourea chloride (9.2 g), m.p. 199°–200° C. (with decomposition).

The N-(2-aminophenyl)-trimethylammonium acetamide chloride used as a starting material in the above preparation was prepared by heating a mixture of N-(2-nitrophenyl)-2-chloroacetamide (32.1 g), a solution of trimethylamine in ethanol (33% w/w; 80 ml) and ethyl acetate (150 ml) under reflux for 1 hour. Petroleum spirit (b.p. 60°–80° C.) was added to the hot solution until it became slightly cloudy. The mixture was then allowed to cool. The precipitated solid (19.5 g), m.p. 120°–124° C., was filtered off, suspended in ethanol (200 ml), platinum oxide catalyst (0.5 g) added and the suspension shaken in an atmosphere of hydrogen at atmosphere pressure and laboratory temperature until 4.8 litres of hydrogen had been absorbed. The mixture was then filtered and ethanol was distilled from the filtrate until a small quantity (about 20 ml) remained. The solid present was filtered off to give N-(2-aminophenyl)-trimethylammoniumacetamide chloride (9.1 g), m.p. 210°–211° C., which was used as starting material in the above preparation without further purification.

EXAMPLE 14

A stirred solution of N-(2-aminophenyl)-2-(2,6-cis-dimethylmorpholino)acetamide (5.4 g) in acetonitrile (50 ml) was treated dropwise with ethoxycarbonyl isothiocyante (2.94 g), the mixture being cooled to 10°–15° C. The solution was stirred at that temperature for twenty minutes and then poured into dry diethyl ether (75 ml). An excess of a solution of hydrogen chloride in diethyl ether was added and the precipitated solid was filtered off and recrystallised from ethanol to give 1-ethoxycarbonyl-3-[2-(2,6-cis-dimethylmorpholinoacetamido)phenyl]thiourea hydrochloride (5.3 g), m.p. 198°–200° C. (with decomposition).

The N-(2-aminophenyl)-2-(2,6-cis-dimethylmorpholino)acetamide, used as a starting material for the above reaction, was prepared as follows:

A mixture of N-(2-nitrophenyl)-2-chloroacetamide (8.6 g), 2,6-cis-dimethylmorpholine (9.2 g) and ethanol (100 ml) was heated together under reflux for 3 hours. The ethanol was evaporated off and the residue treated with water (100 ml). The resultant suspension was filtered and the solid recrystallised from ethanol to give N-(2-nitrophenyl)-2-(2,6-cis-dimethylmorpholino)acetamide (8.5 g), m.p. 127°–129° C. (with decomposition) which was then dissolved in methanol (100 ml). Platinum oxide (0.3 g) was added to the solution which was then shaken in an atmosphere of hydrogen at atmospheric pressure and laboratory temperature until 1.9 litres of hydrogen had been absorbed. The mixture was filtered and the ethanol evaporated off to give a white solid which was recrystallised from water to give N-(2-aminophenyl)-2-(2,6-cisdimethylmorpholino)acetamide (5.4 g), m.p. 104°–106° C. (with decomposition).

EXAMPLE 15

A mixture of 1-methoxycarbonyl-3-(2-aminophenyl)thiourea (10.9 g., 0.048 mole), maleic anhydride (4.7 g; 0.048 mole) and ethanol (200 ml) was boiled under reflux with stirring for one hour. The clear solution was allowed to cool and the crystals which deposited were filtered off. These were recrystallised once from ethanol and once from a mixture of acetone and petroleum spirit (b.p. 60°–80° C.) to give 1-methoxycarbonyl-3-[2-(3-carboxyacrylamido)-phenyl]thiourea (4.4 g) m.p. 170°–173° C. (with decomposition).

By proceeding in a similar manner but replacing the maleic anhydride by the appropriate quantity of succinic anhydride, there was prepared 1-methoxycarbonyl-3-[2-(3-carboxypropionamido)phenyl]thiourea, m.p. 183°–185° C. (with decomposition).

Other compounds of general formula I which may be obtained by the procedure described in the foregoing Examples are:

1-methoxycarbonyl-3-(2-N-methyl-acetamidophenyl)thiourea, m.p. 151°–153° C. (with decomposition), 1-methoxycarbonyl-3-(2-amino-4-methylphenyl)thiourea, m.p. 194°–196° C. (with decomposition), 1-ethoxycarbonyl-3-(2-amino-4-fluorophenyl)-thiourea, m.p. 155°–157° C., 1-ethoxycarbonyl-3-(2-amino-4-chlorophenyl)thiourea, m.p. 169°–171° C. (with decomposition) and 1-butoxycarbonyl-3-(2-aminophenyl)thiourea, m.p. 139°–141° C.

The 1-alkoxycarbonyl-3-(2-nitrophenyl)thiourea starting materials for the preparations described in Example 3 were prepared as follows:

a. Dry potassium thiocyanate (42.8 g; 0.44 mole), methyl chloroformate (37.8 g; 0.40 mole) and dry acetonitrile (130 ml) were mixed with stirring at laboratory temperature and stirring was continued for 1 hour at 35°–45° C. The mixture was then cooled in an ice bath to 15° C. and 4-n-butyl-2-nitroaniline (38.8 g; 0.2 mole) was added in portions with stirring during 15 minutes, the temperature of the stirred reaction mixture being maintained between 15° and 18° C. during the addition. When the addition was complete the mixture was stirred at 15° C. for 2 hours, poured into water (1 litre), and the yellow solid which separated was filtered off and washed with water. This crude product was recrystallised from ethanol to give 1-methoxycarbonyl-3-(4-n-butyl-2-nitrophenyl)thiourea (47.8 g) m.p. 164°–165° C. (with decomposition).

By proceeding in a similar manner but substituting the appropriate quantities of 4-isopropoxycarbonylamino-2-nitroaniline, 4-methoxycarbonylamino-2-nitroaniline and 4-amino-3-nitroacetophenone for the 4-n-butyl-2-nitroaniline, there were prepared 1-methoxycarbonyl-3-(4-isopropoxycarbonylamino-2-nitrophenyl)thiourea, m.p. 180°–181° C. (with decomposition), 1-methoxycarbonyl-3-(4-methoxycarbonylamino-2-nitrophenyl)thiourea m.p. 209°–210° C. (with decomposition) and 1-methoxycarbonyl-3-(4-acetyl-2-nitrophenyl)thiourea m.p. 181°–182° C. (with decomposition), respectively.

b. Dry potassium thiocyanate (18.5 g), ethyl chloroformate (15.6 g) and dry acetonitrile (65 ml) were mixed with stirring at laboratory temperature and stirring was continued for 1 hour at 45°–55° C. The mixture was then cooled in an ice bath to 15° C. and 4-n-butyl-2-nitroaniline (19.0 g) was added in portions with stirring during 15 minutes, the temperature of the stirred reaction mixture being maintained between 15 and 18° C. during the addition. When the addition was complete the mixture was stirred at 15° C. for 2 hours, poured into water (1 litre), and the yellow solid which separated was filtered off and washed with water. This crude product was recrystallised from cyclohexane to give 1-ethoxycarbonyl-3-(4-n-butyl-2-nitrophenyl)thiourea (26.9 g), m.p. 121°–123° C.

By proceeding in a similar manner but substituting the appropriate quantity of 4-isopropoxycarbonylamino-2-nitroaniline for the 4-n-butyl-2-nitroaniline, there was prepared 1-ethoxycarbonyl-3-(4-isopropoxycarbonylamino-2-nitrophenyl)thiourea, m.p. 163°–165° C. (with decomposition).

The 4-isopropoxycarbonylamino-2-nitroaniline and 4-methoxycarbonylamino-2-nitroaniline used as starting materials in the above preparations were produced as follows:

(The other aniline used as starting material in the above preparation is an article of commerce):

A stirred suspension of 2,5-diaminonitrobenzene (60 g.) in a solution of sodium bicarbonate (49.4 g) in water (780 ml) at 10° C. was treated dropwise with isopropyl chloroformate (48 g) and the mixture was stirred at room temperature for 3 hours. The crude brown solid was filtered off, washed well with water and dried to give 4-isopropoxycarbonylamino-2-nitroaniline (90.0 g), m.p. 158°–160° C., which was used in the next stage of the synthesis without further purification being necessary. Recrystallization of a sample from toluene gave pure 4-isopropoxycarbonylamino-2-nitroaniline, m.p. 161°–163° C.

By proceeding in a similar manner, but substituting an equimolecular quantity of methyl chloroformate for the isopropyl chloroformate, there was obtained 4-methoxycarbonylamino-2-nitroaniline, m.p. 171°–172° C.

The following Examples illustrate the formulation of therapeutically useful and fungicidal compositions including benzene derivatives of general formula I.

EXAMPLE 16

Tablets of the formula:

| | |
|---|---|
| 1-Methoxycarbonyl-3-(2-aminophenyl)thiourea | 250 mg. |
| lactose | 200 mg. |
| starch | 50 mg. |
| polyoxyethylene sorbitan monolaurate | 0.5 mg. |
| magnesium stearate | 5 mg. | are prepared by mixing the benzene derivatives and the lactose with part of the starch and granulating with a 5% starch mucilage containing the polyoxyethylene sorbitan monolaurate.

The mixture is sifted through a 20 mesh British Standard sieve, dried, and the remainder of the starch, together with the magnesium stearate, is incorporated into the mixture. After a second sifting through a 20 mesh British Standard sieve the mixture is compressed into tablets.

EXAMPLE 17

1-Methoxycarbonyl-3-(2-aminophenyl)thiourea (1 g), previously sifted through a 40 mesh British Standard sieve, is packed into a gelatin capsule.

The 1-Methoxycarbonyl-3-(2-aminophenyl)thiourea may be replaced by the same quantity of any other compound of general formula I e.g. 1-methoxycarbonyl-3-(2-dimethylaminoacetamidophenyl)thiourea hydrochloride.

EXAMPLE 18

A preparation for oral administration is obtained by mixing 1-methoxycarbonyl-3-(2-aminophenyl)thiourea (1 g), previously sifted through a 40 mesh British Standard sieve, and polyethylene glycol 6000 (10 g) at 50° C., and cooling to 25° C. to obtain a gel.

The 1-methoxycarbonyl-3-(2-aminophenyl)thiourea may be replaced by a similar quantity of any other compound of general formula I, e.g. 1-methoxycarbonyl-3-(2-dimethylaminoacetamidophenyl)thiourea hydrochloride.

EXAMPLE 19

1-Methoxycarbonyl-3-(2-aminophenyl)thiourea (18 parts by weight) is added to wheat middlings (82 parts by weight) and intimately mixed to give a concentrate suitable for incorporation in an animal feedstuff at a rate sufficient to give an anthelmintically-effective amount of the benzene derivative in the feedstuff consumed by the animal. If desired, conventional adhesive agents may be incorporated into the concentrate which may then be compressed into pellets. The pellets may be fed to animals at a rate sufficient to administer an anthelmintically-effective amount of the benzene derivatives to the animal, if desired mixed with an animal feedstuff.

The 1-methoxycarbonyl-3-(2-aminophenyl)thiourea may be replaced by a similar quantity of any other compound of general formula I e.g. 1-methoxycarbonyl-3-(2-dimethylaminoacetamidophenyl)thiourea hydrochloride.

EXAMPLE 20

1-Methoxycarbonyl-3-(2-aminophenyl)thiourea (5 parts by weight) was added to limestone flour (20 parts by weight). The mixture was ground to give a concentrate suitable for incorporation in an animal feedstuff at a rate sufficient to give an anthelmintically-effective amount of the benzene derivative in the feedstuff consumed by the animal.

The 1-methoxycarbonyl-3-(2-aminophenyl)thiourea may be replaced by a similar quantity of any other compound of general formula I, e.g. 1-methoxycarbonyl-3-(2-dimethylaminoacetamidophenyl)thiourea hydrochloride.

EXAMPLE 21

A solution for oral administration as an anthelmintic is obtained by dissolving 1-methoxycarbonyl-3-(2-dimethylaminoacetamidophenyl)thiourea hydrochloride (10 g) and 1-styrylpyridinium isethionate (10 g; prepared as described in British Pat. No. 1,221,061) in water (50 ml). This solution may, if desired, be sterilised by filtration through a bacteria-retaining filter to give a sterile composition suitable for parenteral administration as an anthelmintic.

EXAMPLE 22

A solution for oral administration as an anthelmintic is obtained by dissolving diethylcarbamazine citrate (4.4 g) and 1-methoxycarbonyl-3-(2-dimethylaminoacetamidophenyl)thiourea methanesulphonate (10 g) in water (20 ml). This solution may, if desired, be sterilised by filtration through a bacteria-retaining filter to give a sterile composition suitable for parenteral administration as an anthelmintic.

EXAMPLE 23

A wettable powder is obtained by mixing:

| | |
|---|---|
| 1-methoxycarbonyl-3-(2-dimethylaminoacetamidophenyl)thiourea hydrochloride | 50 parts by weight |
| Texofor FX 500 (an alkylphenol-polyoxyethylene condensate) | 10 parts by weight |
| Celite 281 (a finely-divided diatomaceous earth) | 40 parts by weight | in a ribbon-blender. The powder obtained may be diluted with water and applied at a rate of 2 lbs. of powder in 100 gallons of spray fluid per acre to apple trees as a fungicide to protect them from infections of *Podosphaerea leucotricha*.

EXAMPLE 24

A wettable powder is obtained by mixing:

| | |
|---|---|
| 1-methoxycarbonyl-3-(2-dimethylaminoacetamidophenyl)thiourea hydrochloride | 50 parts by weight |
| Belloid TD (a polymethyl bis-naphthyl sodium sulphonate) | 10 parts by weight |
| Clarcelflo SAS (an expanded pearlite) | 35 parts by weight |
| Aerosil (a finely-divided silicon dioxide) | 5 parts by weight | in a ribbon-blender. The powder obtained may be diluted with water and applied at a rate of 2 lbs. of powder in 20 gallons of spray fluid per acre to barley to protect against infections of Erysiphe graminis.

EXAMPLE 25

A liquid concentrate in the form of a suspension is obtained by mixing:

| | |
|---|---|
| 1-methoxycarbonyl-3-(2-dimethylaminoacetamidophenyl)thiourea hydrochloride | 60 parts by weight |
| bentonite | 3 parts by weight |
| Cutafor 09 (a polyethoxylated-alkylamine) | 10 parts by weight |
| White Spirits (a petroleum distillate) | 10 parts by weight |

The concentrate obtained may be diluted with water and applied at a rate of 1½ lbs. of concentrate in 50 gallons of spray fluid per acre to strawberries to protect them against infections of Botrytis cinerea.

We claim:

1. Method for the treatment of helminth infections in man and domestic animals which comprises administering to man or a domestic animal infected with helminths an anthelmintically effective amount of at least one benzene derivative of the formula:

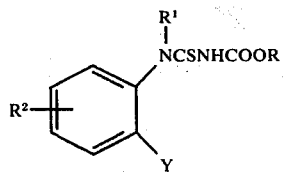

wherein R represents an aliphatic hydrocarbon group of 1 to 4 carbon atoms which is unsubstituted or substituted by halogen or alkoxy of 1 to 4 carbon atoms, $R^1$ represents hydrogen or methyl, $R^2$ represents hydrogen, halogen, alkyl of 1 to 4 carbon atoms, alkanoylamino of 1 to 4 carbon atoms which is unsubstituted or substituted by cycloalkyl of 3 to 6 carbon atoms, alkoxycarbonylamino of 2 to 4 carbon atoms, alkanoyl of 2 to 4 carbon atoms, benzoyl or N-methylmethanesulphonylamino, and Y represents a group —$NR^3R^4$, wherein $R^3$ and $R^4$ each represent hydrogen, or $R^3$ represents hydrogen or methyl and $R^4$ represents alkanoyl of 1 to 4 carbon atoms which is unsubstituted or substituted by cycloalkyl of 3 to 6 carbon atoms, alkoxycarbonyl of 2 to 4 carbon atoms, or a group —COAZ, wherein A represents a straight chain aliphatic hydrocarbon group of 1 to 4 carbon atoms which is unsubstituted or substituted by methyl, and Z represents carboxy or a group of the formula:

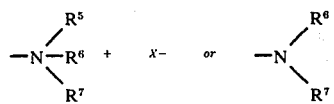

wherein $R^5$ represents hydrogen or alkyl of 1 to 4 carbon atoms, $R^6$ represents hydrogen, alkyl of 1 to 4 carbon atoms or phenylalkyl with 1 or 2 carbon atoms in the alkyl moiety, and $R^7$ represents hydrogen or alkyl of 1 to 4 carbon atoms, and $X^-$ represents a pharmaceutically acceptable anion, or where Y represents a primary amino group, an acid addition salt thereof having a pharmaceutically acceptable anion.

2. Method according to claim 1 in which man or the domestic animal is infected with parasitic nematode worms.

3. Method according to claim 1 in which R is methyl, ethyl, n-butyl, allyl, propargyl, 2-chloroethyl or 2-ethoxyethyl.

4. Method according to claim 1 in which $R^1$ is hydrogen.

5. Method according to claim 1 in which $R^2$ is hydrogen, chlorine, fluorine, methyl, n-butyl, methoxycarbonylamino, ethoxycarbonylamino, isopropoxycarbonylamino or acetyl.

6. Method according to claim 1 in which $R^2$ is hydrogen and Y is primary amino.

7. Method according to claim 1 in which R is methyl or ethyl.

8. Method according to claim 1 in which the dose of benzene derivative administered to man or domestic animal is 5 mg. to 1000 mg. per kilogramme of body weight.

9. Method according to claim 8 in which the dose of benzene derivative administered to man or domestic animal is 25 mg. to 250 mg. per kilogramme of body weight.

10. Method according to claim 1 in which the domestic animals treated are cattle, sheep, pigs, goats, poultry or equines.

11. Method according to claim 1 in which Y is a group —$NR^3R^4$, wherein $R^3$ is hydrogen or methyl and $R^4$ is a group —COAZ, wherein A is a straight chain aliphatic hydrocarbon group of 1 to 4 carbon atoms which is unsubstituted or substituted by methyl, and Z is a group:

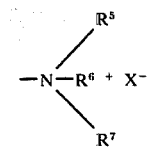

wherein $R^5$ is hydrogen or alkyl of 1 to 4 carbon atoms, $R^6$ is hydrogen, alkyl of 1 to 4 carbon atoms or phenylalkyl with 1 or 2 carbon atoms in the alkyl moiety, and $R^7$ is hydrogen or alkyl of 1 to 4 carbon atoms, and $X^-$ is a pharmaceutically acceptable anion.

12. Method according to claim 11 in which the compound is administered in water.

13. Method according to claim 1 in which R is methyl, $R^1$ and $R^2$ are both hydrogen, and Y is dimethylaminoacetamido.

14. Medicated animal feedstuff comprising an aminal feedstuff and 0.001% to 3% by weight of said feedstuff of a benzene derivative of the formula:

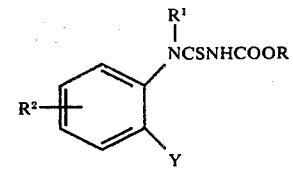

wherein R represents an aliphatic hydrocarbon group of 1 to 4 carbon atoms which is unsubstituted or substituted by halogen or alkoxy of 1 to 4 carbon atoms, $R^1$ represents hydrogen or methyl, $R^2$ represents hydrogen, halogen, alkyl of 1 to 4 carbon atoms, alkanoylamino of 1 to 4 carbon atoms which is unsubstituted or substituted by cycloalkyl of 3 to 6 carbon atoms, alkoxycarbonylamino of 2 to 4 carbon atoms, alkanoyl of 2 to 4 carbon atoms, benzoyl or N-methylmethanesulphonylamino, and Y represents a group —$NR^3R^4$, wherein $R^3$ and $R^4$ each represent hydrogen, or $R^3$ represents hydrogen or methyl and $R^4$ represents alkanoyl of 1 to 4 carbon atoms which is unsubstituted or substituted by cycloalkyl of 3 to 6 carbon atoms, alkoxycarbonyl of 2 to 4 carbon atoms, or a group —COAZ, wherein A represents a straight chain aliphatic hydrocarbon group of 1 to 4 carbon atoms which is unsubstituted or substituted by methyl, and Z represents carboxy or a group of the formula:

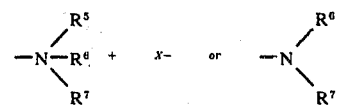

wherein $R^5$ represents hydrogen or alkyl of 1 to 4 carbon atoms, $R^6$ represents hydrogen, alkyl of 1 to 4 carbon atoms or phenylalkyl with 1 or 2 carbon atoms in the alkyl moiety, and R[7] represents hydrogen or alkyl of 1 to 4 carbon atoms, and X[−] represents a pharmaceutically acceptable anion, or where Y represents a primary amino group, an acid addition salt thereof having a pharmaceutically acceptable anion.

15. Medicated animal feedstuff according to claim 14 which include an effective amount of a fasciolicide or an anthelmintic.

16. A method for the treatment of helminth infections in man and domestic animals which comprises administering to man or a domestic animal infected with helminths an anthelmintically effective amount of at least one benzene derivative of the formula:

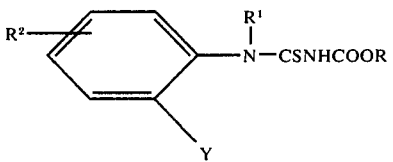

wherein R represents an aliphatic hydrocarbon group of 1 to 4 carbon atoms which is unsubstituted or substituted by halogen or alkoxy of 1 to 4 carbon atoms, R[1] represents hydrogen or methyl, R[2] represents hydrogen, halogen, alkyl of 1 to 4 carbon atoms, and Y represents the group

and a pharmaceutically acceptable acid addition salt thereof.

* * * * *